US009933443B2

(12) United States Patent
Kumano et al.

(10) Patent No.: US 9,933,443 B2
(45) Date of Patent: Apr. 3, 2018

(54) METHOD, APPARATUS, AND COMPUTER PROGRAM FOR BLOOD SAMPLE DETERMINATION, AND BLOOD SAMPLE ANALYZER

(71) Applicants: SCHOOL JURIDICAL PERSON HIGASHI-NIPPON-GAKUEN, Ishikari-gun, Hokkaido (JP); SYSMEX CORPORATION, Kobe-shi, Hyogo (JP)

(72) Inventors: Osamu Kumano, Kobe (JP); Naohiko Matsuo, Kobe (JP); Nobuo Arai, Kobe (JP); Masahiro Ieko, Ishikari-gun (JP)

(73) Assignees: SCHOOL JURIDICAL PERSON HIGASHI-NIPPON-GAKUEN, Ishikari-gun, Hokkaido (JP); SYSMEX CORPORATION, Kobe-shi, Hyogo (JP)

( * ) Notice: Subject to any disclaimer, the term of this patent is extended or adjusted under 35 U.S.C. 154(b) by 53 days.

(21) Appl. No.: 15/082,170

(22) Filed: Mar. 28, 2016

(65) Prior Publication Data

US 2016/0291042 A1 Oct. 6, 2016

(30) Foreign Application Priority Data

Mar. 31, 2015 (JP) .................. 2015-073618

(51) Int. Cl.
*G01N 33/86* (2006.01)
*G01N 21/77* (2006.01)
*G01N 33/49* (2006.01)
*G01N 21/82* (2006.01)
*G01N 15/14* (2006.01)
*G01N 21/51* (2006.01)

(52) U.S. Cl.
CPC ............. *G01N 33/86* (2013.01); *G01N 21/77* (2013.01); *G01N 21/82* (2013.01);
(Continued)

(58) Field of Classification Search
CPC .... G01N 33/86; G01N 33/4905; G01N 21/77; G01N 21/82; G01N 21/51;
(Continued)

(56) References Cited

U.S. PATENT DOCUMENTS 4,454,752 A 6/1984 Scordato
6,898,532 B1 * 5/2005 Toh .................... G01N 33/4905
702/19

(Continued)

FOREIGN PATENT DOCUMENTS

EP 2 722 675 A1 4/2014
EP 2 775 292 A1 9/2014

OTHER PUBLICATIONS

Collins, Peter et al. "Consensus recommendations for the diagnosis and treatment of acquired hemophilia A." BMC Research Notes (2010) 3 161.*

(Continued)

*Primary Examiner* — Christopher Adam Hixson
(74) *Attorney, Agent, or Firm* — Sughrue Mion, PLLC

(57) ABSTRACT

Disclosed is a blood sample determination method including: preparing a mixed plasma by mixing a subject plasma and a normal plasma; emitting light to a measurement specimen obtained by mixing the mixed plasma and a clotting time measuring reagent, to obtain optical information regarding an amount of light from the measurement specimen; and determining whether the subject plasma is suspected to be a coagulation-factor-deficient plasma, on the basis of optical information obtained from one measurement specimen.

21 Claims, 24 Drawing Sheets

(52) U.S. Cl.
CPC ..... G01N 33/4905 (2013.01); *G01N 15/1456* (2013.01); *G01N 21/51* (2013.01); *G01N 2015/1488* (2013.01); *G01N 2021/825* (2013.01); *G01N 2201/061* (2013.01)

(58) Field of Classification Search
CPC .......... G01N 2201/061; G01N 15/456; G01N 2015/1488; G01N 2021/825
See application file for complete search history.

(56) References Cited

U.S. PATENT DOCUMENTS

| | | | |
|---|---|---|---|
| 7,074,582 B2 * | 7/2006 | Fischer | G01N 33/86 435/13 |
| 2003/0104493 A1 | 6/2003 | Ortel et al. | |
| 2013/0344519 A1 | 12/2013 | Leong et al. | |

OTHER PUBLICATIONS

Matsumoto, T. et al. "The measurement of low levels of factor VIII or factor IX in hemophilia A and hemophilia B plasma by clot waveform analysis and thrombin generation assay." Journal of Thrombosis and Haemostasis (2006) 4 377.*

Shima M. et al. "Towards standardization of clot waveform analysis and recommenations for its clinical applicaitons." Journal of Thrombosis and Haemostasis (2013) 11 1417.*

* cited by examiner

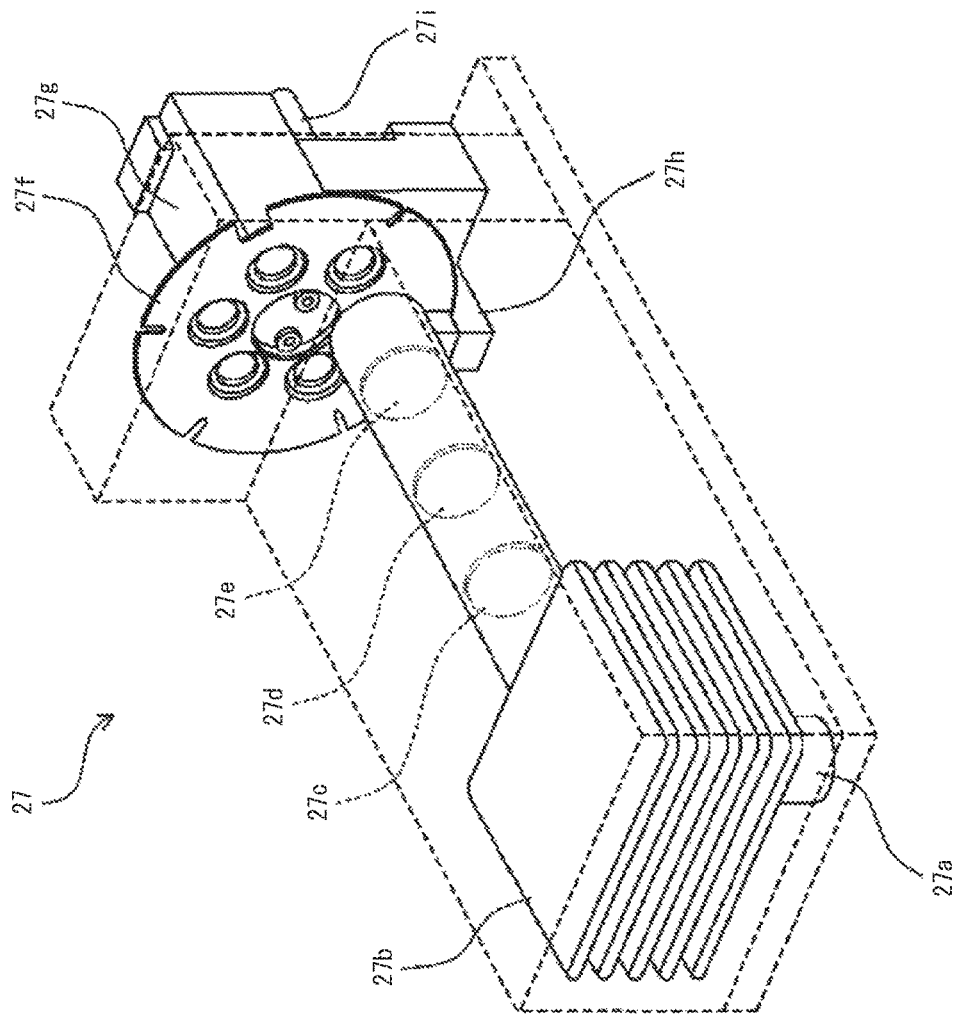

METHOD, APPARATUS, AND COMPUTER PROGRAM FOR BLOOD SAMPLE DETERMINATION, AND BLOOD SAMPLE ANALYZER

CROSS REFERENCE TO RELATED APPLICATIONS

This application claims priority from prior Japanese Patent Application No. 2015-073618, filed on Mar. 31, 2015, entitled "Method, apparatus, and computer program for blood sample determination, and blood sample analyzer", the entire content of which is incorporated herein by reference.

FIELD OF THE INVENTION

The present invention relates to a method for blood sample determination. The present invention also relates to an apparatus and a computer program for blood sample determination. Further, the present invention relates to a blood sample analyzer.

BACKGROUND

Coagulation test, which is one type of blood test, is conducted by measuring clotting time of blood in order to grasp the state of hemostasis mechanism. When prolongation of clotting time is observed, congenital coagulation disorder due to congenital deficiency or abnormality in blood coagulation factors, or acquired coagulation inhibition due to autoantibodies that inhibit coagulation reaction is suspected as the cause of the prolongation. Congenital coagulation disorder can be distinguished from acquired coagulation inhibition on the basis of a test (cross-mixing test) that measures clotting time of a specimen prepared by mixing a normal plasma and a subject plasma that shows prolongation of clotting time. That is, in the case of congenital coagulation disorder, prolongation of clotting time is corrected by the subject plasma being mixed with the normal plasma, but in the case of acquired coagulation disorder, prolongation of clotting time is not corrected.

In a cross-mixing test, clotting times of a specimen that has just been prepared and a specimen incubated at 37° C. for 2 hours are respectively measured, and on the basis of change in the pattern of a graph on which the obtained clotting times of the respective specimens and mixing ratios of the normal plasma and the subject plasma are plotted, a sample that contains coagulation factor inhibitors or lupus anticoagulant (LA) which are autoantibodies is distinguished from a sample derived from a coagulation factor deficient patient. However, making such distinction by finding the difference in pattern change on the graph requires experience, and there are many cases where only experts can see such difference.

In recent years, for assessment of the entire process from the start of clotting to formation of fibrin clots, analysis of clot waveform has been attracting attention. The clot waveform is a waveform that represents temporal change in optical characteristics such as transmission and scatter of light in the blood sample, the change occurring in accordance with advancement of blood sample clotting. Through the analysis of the clot waveform, information such as velocity and acceleration of coagulation is obtained. For example, U.S. Patent Application Publication No. 2003/0104493 indicates that patients having antiphospholipid antibodies (including IA) and receiving warfarin show maximum coagulation acceleration and maximum coagulation deceleration that are different from those of healthy individuals.

As described above, a coagulation-factor-deficient sample can be distinguished from a blood sample containing coagulation factor inhibitors or LA through a cross-mixing test, which is, however, not quantitative assessment. Further, the cross-mixing test requires a plurality of measurement specimens prepared by mixing a subject plasma and a normal plasma at various ratios, and thus, when the amount of the subject plasma is small, the cross-mixing test cannot be conducted. Therefore, there is a demand for measures that can quantitatively determine whether the blood sample is suspected to be a coagulation-factor-deficient sample, on the basis of measurement data from one measurement specimen.

SUMMARY OF THE INVENTION

The scope of the present invention is defined solely by the appended claims, and is not affected to any degree by the statements within this summary.

BRIEF DESCRIPTION OF THE DRAWINGS

FIG. 5 shows a configuration of a lamp unit provided in a measurement apparatus;

DETAILED DESCRIPTION OF THE PREFERRED EMBODIMENTS

[1. Blood Sample Determination Method]

Figure 1:
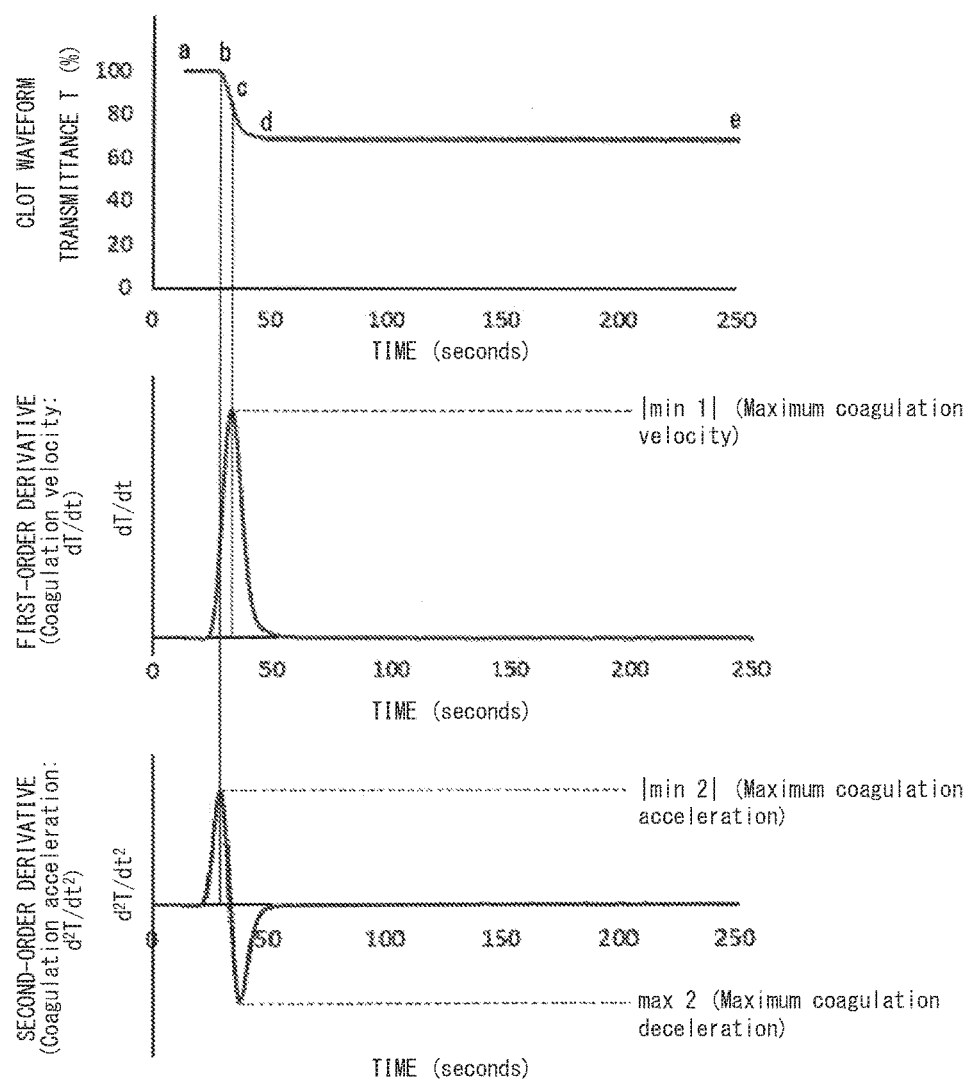
FIG. 1 is one example of a clot waveform of a normal plasma and graphs of a first-order derivative thereof and a second-order derivative thereof.

In a blood sample determination method (hereinafter, also simply referred to as "method") according to a first mode, first, a mixed plasma is prepared by mixing a subject plasma and a normal plasma.

In the present embodiment, a subject plasma which is a blood sample on which the determination is performed is not particularly limited as long as the subject plasma is plasma derived from a subject, but preferably is a plasma derived from a subject suspected to have coagulation abnormality. Examples of the subject plasma for which coagulation abnormality is suspected include a plasma for which prolongation of clotting time has been observed in an ordinary coagulation test, and a group of samples obtained from a plurality of subjects including individuals suspected to have coagulation abnormality. As the plasma, a plasma from which platelets have been removed is preferable in particular. Platelets can be removed by a known technique such as a centrifugation or filtering.

In the present embodiment, causes of coagulation abnormality are not particularly limited, but examples thereof include coagulation factor deficiencies, the presence of coagulation factor inhibitors, the presence of LA, and receiving drugs that act on blood coagulation. Coagulation factors whose deficiency is suspected are not particularly limited, but examples thereof include factor V, factor VII, factor VIII, factor IX, factor X, factor XI, and factor XII. Herein, "coagulation factor deficiency" means that normal coagulation factors are absent or very few in blood. In addition, herein, the concept "coagulation factor deficiency" also includes coagulation factor abnormalities. Examples of the coagulation factor abnormalities include lack of activity.

In the present embodiment, coagulation factor inhibitors are not particularly limited, but examples thereof include factor VIII inhibitor, factor IX inhibitor, and factor V inhibitor. Drugs that act on blood coagulation are not particularly limited, but examples thereof include heparin and warfarin.

A normal plasma may be any plasma prepared from blood obtained from a healthy individual, or a commercially available normal plasma. Examples of the commercially available normal plasma include CRYOcheck Pooled Normal Plasma (Precision BioLogic Inc).

The method according to the present embodiment is based on the principle of cross-mixing test, and thus, a sample (mixed plasma) obtained by mixing a subject plasma and a normal plasma with at least one mixing ratio is used. In the present embodiment, a mixed plasma is a blood sample that is to be measured. The mixing ratio of the subject plasma and the normal plasma can be determined as appropriate in accordance with the amount of the subject plasma and the like. For example as the proportion of the subject plasma in the mixed plasma, at least one can be selected from among 10, 20, 30, 40, 50, 60, 70, 80, and 90% (v/v). Among these, it is preferable to prepare a mixed plasma in which the proportion of the subject plasma is 50% (v/v). There may be one or a plurality of mixed plasmas for one subject plasma. The mixing operation may be conducted manually, or by a fully automatic clotting time measurement apparatus.

In the method according to the present embodiment, a measurement specimen obtained by mixing the thus-obtained mixed plasma with a clotting time measuring reagent is irradiated with light, and optical information regarding the amount of light is obtained from the measurement specimen.

In the present embodiment, the clotting time measuring reagent (hereinafter, also simply referred to as "reagent") may be any reagent for measuring clotting time based on a known measurement principle in this technical field. Examples thereof include a reagent for measuring at least one of prothrombin time (PT), activated partial thromboplastin time (APTT), dilute prothrombin time (dPT), dilute activated partial thromboplastin time (dAPTT), kaolin clotting time (KCT), dilute Russell viper venom clotting time (dRVVT), thrombin time (TT), and dilute thrombin time (dTT). Among these, a dAPTT measuring reagent is preferable. A commercially available clotting time measuring reagent and a commercially available reagent kit may be used. For example, as the APTT measuring reagent, Thrombocheck APTT-SLA (Sysmex Corporation), Thrombocheck APTT (Sysmex Corporation), Actin FSL (Sysmex Corporation), and the like are known.

In the present embodiment, the measurement specimen may be prepared by mixing a plasma and a reagent by a known technique in accordance with the measurement principle of the reagent to be used. For example, the reaction time of the reaction between the plasma and the reagent is normally not shorter than 1 minute and not longer than 10 minutes, and preferably not shorter than 3 minutes and not longer than 5 minutes. The temperature condition is normally not lower than 25° C. and not higher than 45° C., and preferably not lower than 35° C. and not higher than 38° C. The measurement specimen may be prepared manually or by a fully automatic clotting time measurement apparatus, but is preferably prepared by a fully automatic clotting time measurement apparatus. Examples of the fully automatic clotting time measurement apparatus include CS-5100 (Sysmex Corporation), CS-2400 (Sysmex Corporation), and CS-2000i (Sysmex Corporation). There may be one or a plurality of measurement specimens for one subject plasma.

In the present embodiment, light to be emitted to the measurement specimen may be any light that is usually used in measurement of clotting time, and examples thereof include light whose wavelength is about 660 m, preferably 660 nm. The light source thereof is not particularly limited, but examples thereof include a light emitting diode and a halogen lamp.

By the light source emitting light to the measurement specimen, scattered light and transmitted light occur from the measurement specimen. In the present embodiment, examples of optical information regarding the amount of light include information regarding the amount of scattered light or the amount of transmitted light. Scattered light intensity, transmittance, absorbance, and the like are preferable.

In the present embodiment, the measurement condition is not particularly limited, but preferably, emission of light and obtainment of optical information regarding the amount of light are continuously or intermittently performed from the start of the measurement (from the mixing of the plasma and the reagent) until the end of the coagulation reaction (formation of fibrin clots). On the basis of the optical information regarding the amount of light (for example, scattered light intensity, transmittance, or absorbance) continuously or intermittently measured through the entire process of the coagulation, it is possible to obtain parameters regarding derivative of clot waveform described later, at a desired time point or during a desired time period in the coagulation process. Emission of light and obtainment of optical information regarding the amount of light may be performed by a fully automatic measurement apparatus. Examples of such an apparatus include the CS series (Sysmex Corporation) of fully automatic blood coagulation measurement apparatuses.

In a conventional cross-mixing test, it is observed how the clotting time of the mixed plasma changes when the proportion of the subject plasma in the mixed plasma is changed, and the cause of coagulation abnormality of the subject plasma is determined. Thus, in the conventional cross-mixing test, for the determination, it is necessary to mix the subject plasma and the normal plasma at various ratios to prepare a plurality of measurement specimens, and then, obtain the clotting times of these. In contrast, in the method according to the present embodiment, as described later, it is possible to perform the determination on the subject plasma on the basis of optical information obtained from one measurement specimen.

In the present embodiment, in the case where there is one subject plasma, one measurement specimen may be prepared from a mixed plasma prepared from the subject plasma. When a plurality of mixed plasmas are prepared from one subject plasma, from which mixed plasma one measurement specimen is to be prepared is not particularly limited. In the present embodiment, in the case where there are a plurality of subject plasmas, one measurement specimen derived from each subject plasma may be prepared from a mixed plasma prepared from the subject plasma. That is, for each of the plurality of subject plasmas, one measurement specimen that is paired with the subject plasma is prepared. Among the mixed plasmas prepared from the plurality of subject plasmas, the mixing ratio between each subject plasma and the normal plasma may be the same or different, but preferably the same.

In the method according to the present embodiment, whether the above-described subject plasma is suspected to be a coagulation-factor-deficient plasma is determined on the basis of the optical information obtained from one measurement specimen. In the present embodiment, when there are a plurality of measurement specimens for one subject plasma, optical information obtained from any one of the measurement specimens may be used in the determination.

In a preferable embodiment, at least one parameter regarding derivative of clot waveform is obtained on the basis of optical information obtained from one measurement specimen. In the present embodiment, the clot waveform is a waveform that represents temporal change in optical information regarding the amount of light (for example, the amount of scattered light, transmittance, or absorbance). With reference to FIG. 1, the clot waveform and analysis of the waveform will be described. In the clot waveform (the uppermost graph) in FIG. 1, Point a indicates the measurement start point, and Point b indicates the fibrin deposition (coagulation start) point, and a-b indicates the clotting time. Point c is the midpoint of the coagulation, Point d is the end point of the coagulation, and Point e is the end point of the measurement. When derivative (first-order derivative) of the clot waveform is taken, coagulation velocity is calculated (see the middle graph in FIG. 1). It should be noted that Point c in the clot waveform corresponds to the maximum value of the first-order derivative. When derivative (second-order derivative) of the coagulation velocity is taken, coagulation acceleration is calculated (see the lowermost graph in FIG. 1). In the method according to the present embodiment, the clotting time and the clot waveform may be or may not be obtained.

In the present embodiment, each parameter regarding derivative of clot waveform is not particularly limited as long as the parameter is a value that indicates at least one of coagulation velocity, coagulation acceleration, and coagulation deceleration, which are obtained on the basis of optical information obtained from one measurement specimen. Here, the value indicating the coagulation velocity corresponds to a value that can be obtained from the first-order derivative of a clot waveform, and the value indicating the coagulation acceleration and the value indicating the coagulation deceleration correspond to values that can be obtained from the second-order derivative of the clot waveform. Examples of such a parameter include |min 1|, |min 2|, and max 2. The |min 1| is the absolute value of the minimum value of the first-order derivative of the clot waveform, and represents maximum coagulation velocity. The |min 2| is the absolute value of the minimum value of the second-order derivative of the clot waveform, and represents maximum coagulation acceleration. The max 2 is the maximum value of the second-order derivative of the clot waveform, and represents maximum coagulation deceleration. The terms |min 1|, |min 2|, and max 2 themselves are known in this technical field. The parameter regarding derivative of clot waveform may be a value that can be obtained by combining two or more of these values, and examples of such a parameter include the sum, the difference, the product, and the ratio of at least two values selected from |min 1|, |min 2|, and max 2.

When clotting time has also been obtained from the same measurement specimen, the parameter regarding derivative of clot waveform may be a value obtained by combining the clotting time and the value that is obtained from the first-order derivative or the second-order derivative of the clot waveform. Examples of such a value include the sum, the difference, the product, and the ratio of the value of the clotting time and at least one value selected from |min 1|, |min 2|, and max 2.

In the present embodiment, whether the subject plasma is suspected to be a coagulation-factor-deficient plasma can be determined on the basis of the value of the obtained parameter. Preferably, the determination is made on the basis of the result of comparison of the value of the obtained parameter with a predetermined threshold corresponding to the parameter. For example, the value of |min 1| is compared with a first threshold in the case where |min 1| has been obtained, the value of |min 2| is compared with a second threshold in the case where |min 2| has been obtained, and the value of max 2 is compared with a third threshold in the case where max 2 has been obtained. Then, on the basis of the result of the comparison, the determination can be made. Specifically, when at least one of the values that have been obtained from among |min 1|, |min 2|, and max 2 is greater than or equal to the predetermined threshold corresponding to that value, it can be determined that the subject plasma is suspected to be a coagulation-factor-deficient plasma. On the other hand, when all the values that have been obtained from among |min 1|, |min 2|, and max 2 are smaller than the predetermined thresholds corresponding to those values, respectively, it can be determined that the subject plasma is suspected to be a plasma having a cause of coagulation abnormality other than coagulation factor deficiency.

In the case where any one of |min 1|, |min 2|, and max 2 has been obtained as the parameter regarding derivative of clot waveform, the determination can be made as follows, for example.

The value of |min 1| is compared with the first threshold. Then, when the value of |min 1| is greater than or equal to the first threshold, it is determined that the subject plasma is suspected to be a coagulation-factor-deficient plasma. On the other hand, when the value of |min 1| is smaller than the first threshold, it is determined that the subject plasma is suspected to be a plasma having a cause of coagulation abnormality other than coagulation factor deficiency.

The value of |min 2| is compared with the second threshold. Then, when the value of |min 2| is greater than or equal to the second threshold, it is determined that the subject plasma is suspected to be a coagulation-factor-deficient plasma. On the other hand, when the value of |min 2| is smaller than the second threshold, it is determined that the subject plasma is suspected to be a plasma having a cause of coagulation abnormality other than coagulation factor deficiency.

The value of max 2 is compared with the third threshold. Then, when the value of max 2 is greater than or equal to the third threshold, it is determined that the subject plasma is suspected to be a coagulation-factor-deficient plasma. On the other hand, when the value of max 2 is smaller than the third threshold, it is determined that the subject plasma is suspected to be a plasma having a cause of coagulation abnormality other than coagulation factor deficiency.

In the case where any two of |min 1|, |min 2|, and max 2 have been obtained as the parameter regarding derivative of clot waveform, the determination can be made as follows, for example.

The value of |min 1| is compared with the first threshold, and the value of min 2| is compared with the second threshold. Then, when the value of |min 1| is greater than or equal to the first threshold, or the value of |min 2| is greater than or equal to the second threshold, it is determined that the subject plasma is suspected to be a coagulation-factor-deficient plasma. On the other hand, when the value of |min 1| is smaller than the first threshold, and the value of |min 2| is smaller than the second threshold, it is determined that the subject plasma is suspected to be a plasma having a cause of coagulation abnormality other than coagulation factor deficiency.

The value of |min 1| is compared with the first threshold, and the value of max 2 is compared with the third threshold. Then, when the value of |min 1| is greater than or equal to the first threshold, or the value of max 2 is greater than or equal to the third threshold, it is determined that the subject plasma is suspected to be a coagulation-factor-deficient plasma. On the other hand, when the value of |min 1| is smaller than the first threshold, and the value of max 2 is smaller than the third threshold, it is determined that the subject plasma is suspected to be a plasma having a cause of coagulation abnormality other than coagulation factor deficiency.

The value of |min 2| is compared with the second threshold, and the value of max 2 is compared with the third threshold. Then, when the value of |min 2| is greater than or equal to the second threshold, or the value of max 2 is greater than or equal to the third threshold, it is determined that the subject plasma is suspected to be a coagulation-factor-deficient plasma. On the other hand, when the value of |min 2| is smaller than the second threshold, and the value of max 2 is smaller than the third threshold it is determined that the subject plasma is suspected to be a plasma having a cause of coagulation abnormality other than coagulation factor deficiency.

In the case where three of |min 1|, |min 2|, and max 2 have been obtained as the parameter regarding derivative of clot waveform, the determination can be made as follows, for example. The value of |min 1| is compared with the first threshold, the value of |min 2| is compared with the second threshold, and the value of max 2 is compared with the third threshold. Then, when the value of |min 1| is greater than or equal to the first threshold, or the value of |min 2| is greater than or equal to the second threshold, or the value of max 2 is greater than or equal to the third threshold, it is determined that the subject plasma is suspected to be a coagulation-factor-deficient plasma. On the other hand, when the value of |min 1| is smaller than the first threshold, and the value of |min 2| is smaller than the second threshold, and the value of max 2 is smaller than the third threshold, it is determined that the subject plasma is suspected to be a plasma having a cause of coagulation abnormality other than coagulation factor deficiency.

In the present embodiment, the predetermined thresholds corresponding to the respective parameters such as the first threshold, the second threshold, and the third thresholds are not particularly limited. For example, by accumulating data of various parameters regarding derivative of clot waveform with respect to coagulation-factor-deficient samples, LA positive samples, and coagulation-factor-inhibitor positive samples, thresholds corresponding to the respective parameters can be empirically set. Alternatively, with respect to each of a group of coagulation-factor-deficient samples, and a group of samples having causes of coagulation abnormality other than coagulation factor deficiency, values of various parameters regarding derivative of clot waveform may be obtained, and then, values that each can clearly distinguish the groups from each other may be set as the predetermined thresholds.

In another embodiment, the clotting time of the subject plasma is obtained in addition to the parameter regarding derivative of clot waveform with respect to the mixed plasma. Then, with respect to a subject plasma for which prolongation of clotting time is observed, the above determination can be made. In this embodiment, on the basis of the clotting time, it is possible to select and determine a subject plasma for which coagulation abnormality is suspected. A blood sample determination method according to this embodiment (second mode) will be described below.

In the method according to the present embodiment, first, a subject plasma and a normal plasma are mixed to prepare a mixed plasma. The subject plasma and the normal plasma are the same as those described with regard to the method according to the first mode.

Next, in the method according to the present embodiment, light is emitted to a first measurement specimen obtained by mixing a subject plasma and a clotting time measuring reagent, and a second measurement specimen obtained by mixing a mixed plasma and a clotting time measuring reagent, and optical information regarding the amount of light from each of the first and second measurement specimens is obtained. The first measurement specimen can be prepared in the same manner as in the case of the measurement specimen in the method according to the first mode except that the subject plasma is used instead of the mixed plasma. In the present embodiment, details of the clotting time measuring reagent and preparation of the second measurement specimen, and obtainment of optical information regarding the amount of light are the same as those described with regard to the method according to the first mode.

In the present embodiment, the clotting time of the first measurement specimen is obtained on the basis of the optical information obtained from the first measurement specimen, and at least one parameter regarding derivative of clot waveform of the second measurement specimen is obtained on the basis of the optical information obtained from one second measurement specimen. Details of obtainment of the parameter regarding derivative of clot waveform are the same as those described with regard to the method according to the first mode. Here, the method itself for obtaining the clotting time of the first measurement specimen (that is, the clotting time of the subject plasma) is known in this technical field. Thus, persons skilled in the art can obtain as appropriate the clotting time of the first measurement specimen, in accordance with the measurement principle of the clotting time measuring reagent to be used.

In the present embodiment, with respect to a subject plasma for which prolongation of the clotting time has been observed, whether the subject plasma is suspected to be a coagulation-factor-deficient plasma can be determined on the basis of the value of the obtained parameter. Details of the procedure of the determination and the predetermined thresholds corresponding to the respective parameters are the same as those described with regard to the method according to the first mode.

In the present embodiment, preferably, whether the first measurement specimen has a prolonged clotting time is determined on the basis of the result of comparison of the obtained clotting time with a predetermined time. For example, when the obtained clotting time is longer than the predetermined time, it can be determined that the subject plasma is a plasma for which prolongation of the clotting time is observed. On the other hand, when the obtained clotting time is not loner than the predetermined clotting time, it can be determined that the subject plasma is a plasma for which prolongation of the clotting time is not observed.

Preferably, the predetermined time is the clotting time of a normal plasma. Examples of the normal plasma include a plasma derived from a healthy individual, or a commercially available normal plasma. The clotting time of such a normal plasma may be the clotting time thereof actually measured in the same manner as in the case of the subject plasma. Alternatively, the clotting time of such a normal plasma may be a clotting time known as a normal value or a reference value for the measurement principle of the clotting time measuring reagent to be used.

In the present embodiment, it is considered that the subject plasma for which prolongation of the clotting time is not observed is not suspected as having coagulation abnormality.

In the method according to the first or second mode described above, when it has been determined that the subject plasma is suspected to be a plasma having a cause of coagulation abnormality other than coagulation factor deficiency, information regarding LA or coagulation factor inhibitors in the subject plasma can be further obtained on the basis of the value of the obtained parameter.

For example, the value of |min 1| is compared with a fourth threshold in the case where |min 1| has been obtained, the value of |min 2| is compared with a fifth threshold in the case where |min 2| has been obtained, and the value of max 2 is compared with a sixth threshold in the case where max 2 has been obtained. Then, on the result of the comparison, whether the subject plasma is suspected to be a plasma containing LA, or whether the subject plasma is suspected to be a plasma containing a coagulation factor inhibitor can be determined. Specifically, when at least one of the values that have been obtained from among |min 1|, |min 21, and max 2 is greater than or equal to the predetermined threshold corresponding to that value, it can be determined that the subject plasma is suspected to be a plasma containing LA. On the other hand, when all the values that have been obtained from among |min 1|, |min 2|, and max 2 are smaller than the predetermined thresholds corresponding to those values, respectively, it can be determined that the subject plasma is suspected to be a plasma containing a coagulation factor inhibitor.

In the case where any one of |min 1|, |min 2| and max 2 has been obtained as the parameter regarding derivative of clot waveform, the determination can be made as follows, for example.

The value of |min 1| is compared with the fourth threshold. Then, when the value of |min 1| is greater than or equal to the fourth threshold, it is determined that the subject plasma is suspected to be a plasma containing LA. On the other hand, when the value of |min 1| is smaller than the fourth threshold, it is determined that the subject plasma is suspected to be a plasma containing a coagulation factor inhibitor.

The value of |min 2| is compared with the fifth threshold. Then, when the value of |min 2| is greater than or equal to the fifth threshold, it is determined that the subject plasma is suspected to be a plasma containing LA. On the other hand, when the value of |min 2| is smaller than the fifth threshold, it is determined that the subject plasma is suspected to be a plasma containing a coagulation factor inhibitor.

The value of max 2 is compared with the sixth threshold. Then, when the value of max 2 is greater than or equal to the sixth threshold, it is determined that the subject plasma is suspected to be a plasma containing LA. On the other hand, when the value of max 2 is smaller than the sixth threshold, it is determined that the subject plasma is suspected to be a plasma containing a coagulation factor inhibitor.

In the case where any two of |min 1|, |min 2|, and max 2 have been obtained as the parameter regarding derivative of clot waveform, the determination can be made as follows, for example.

The value of |min 1| is compared with the fourth threshold, and the value of |min 2| is compared with the fifth threshold. Then, when the value of |min 1| is greater than or equal to the fourth threshold, or the value of min 2, is greater than or equal to the fifth threshold, it is determined that the subject plasma is suspected to be a plasma containing LA. On the other hand, when the value of |min 1| is smaller than the fourth threshold, and the value of |min 2| is smaller than the fifth threshold, it is determined that the subject plasma is suspected to be a plasma containing a coagulation factor inhibitor.

The value of |min 1| is compared with the fourth threshold, and the value of max 2 is compared with the sixth threshold. Then, when the value of |min 1| is greater than or equal to the fourth threshold, or the value of max 2 is greater than or equal to the sixth threshold, it is determined that the subject plasma is suspected to be a plasma containing LA. On the other hand, when the value of |min 1| is smaller than the fourth threshold, and the value of max 2 is smaller than the sixth threshold, it is determined that the subject plasma is suspected to be a plasma containing a coagulation factor inhibitor.

The value of |min 2| is compared with the fifth threshold, and the value of max 2 is compared with the sixth threshold. Then, when the value of |min 2| is greater than or equal to the fifth threshold, or the value of max 2 is greater than or equal to the sixth threshold, it is determined that the subject plasma is suspected to be a plasma containing LA. On the other hand, when the value of |min 2| is smaller than the fifth threshold, and the value of max 2 is smaller than the sixth threshold, it is determined that the subject plasma is suspected to be a plasma containing a coagulation factor inhibitor.

In the case where three of |min 1|, |min 2|, and max 2 have been obtained as the parameter regarding derivative of clot waveform, the determination can be made as follows, for example. The value of |min 1| is compared with the fourth threshold, the value of |min 2| is compared with the fifth threshold, and the value of max 2 is compared with the sixth threshold. Then, when the value of |min 1| is greater than or equal to the fourth threshold, or the value of |min 2| is greater than or equal to the fifth threshold, or the value of max 2 is greater than or equal to the sixth threshold, it is determined that the subject plasma is suspected to be a plasma containing LA. On the other hand, when the value of |min 1| is smaller than the fourth threshold, and the value of |min 2| is smaller than the fifth threshold, and the value of max 2 is smaller than the sixth threshold, it is determined that the subject plasma is suspected to be a plasma containing a coagulation factor inhibitor.

In the present embodiment, the predetermined thresholds corresponding to the respective parameters such as the fourth, fifth, and sixth thresholds are not particularly limited. For example, by accumulating data of various parameters regarding derivative of clot waveform with respect to LA positive samples and coagulation-factor-inhibitor positive samples, these thresholds corresponding to the respective parameters can be empirically set. Alternatively, with respect to each of a group of LA positive samples and a group of coagulation-factor-inhibitor positive samples, values of various parameters regarding derivative of clot waveform may be obtained, and then, values that each can clearly distinguish the groups from each other may be set as the predetermined thresholds.

[2. Blood Sample Analyzer, Apparatus and Computer Program for Blood Sample Determination]

Figure 2:
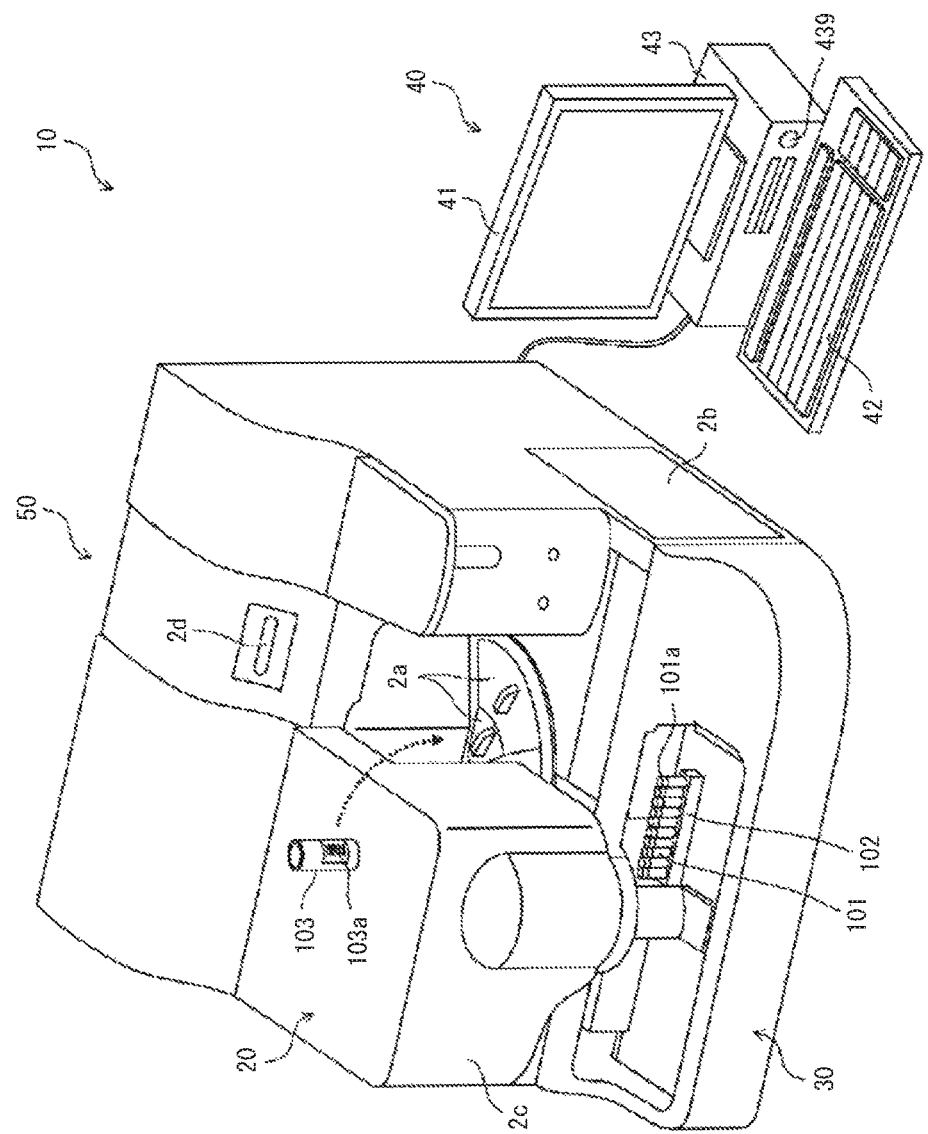
FIG. 2 is a perspective view showing an external structure of a blood sample analyzer.

One example of a blood sample analyzer according to the present embodiment will be described with reference to the drawings. However, the present embodiment is not limited to this example only. As shown in FIG. 2, a blood sample analyzer 10 includes: a measurement apparatus 50 which performs preparation and optical measurement of a measurement specimen; and a control apparatus 40 which analyzes measurement data obtained by the measurement apparatus 50 and which gives instructions to the measurement apparatus 50. The measurement apparatus 50 includes: a measurement unit 20 which obtains optical information regarding the amount of light from the measurement specimen; and a sample transport unit 30 disposed to the front of the measurement unit 20.

The measurement unit 20 is provided with lids 2a and 2b, a cover 2c, and a power button 2d. A user can open the lid 2a to replace reagent containers 103 set on reagent tables 11 and 12 (see FIG. 3) with new reagent containers 103, or to newly add other reagent containers 103. Each reagent container 103 has a bar code label 103a attached thereto. On the bar code label 103a, a bar code including the kind of the reagent contained therein and a reagent ID composed of a serial number given to the reagent is printed.

Figure 3:
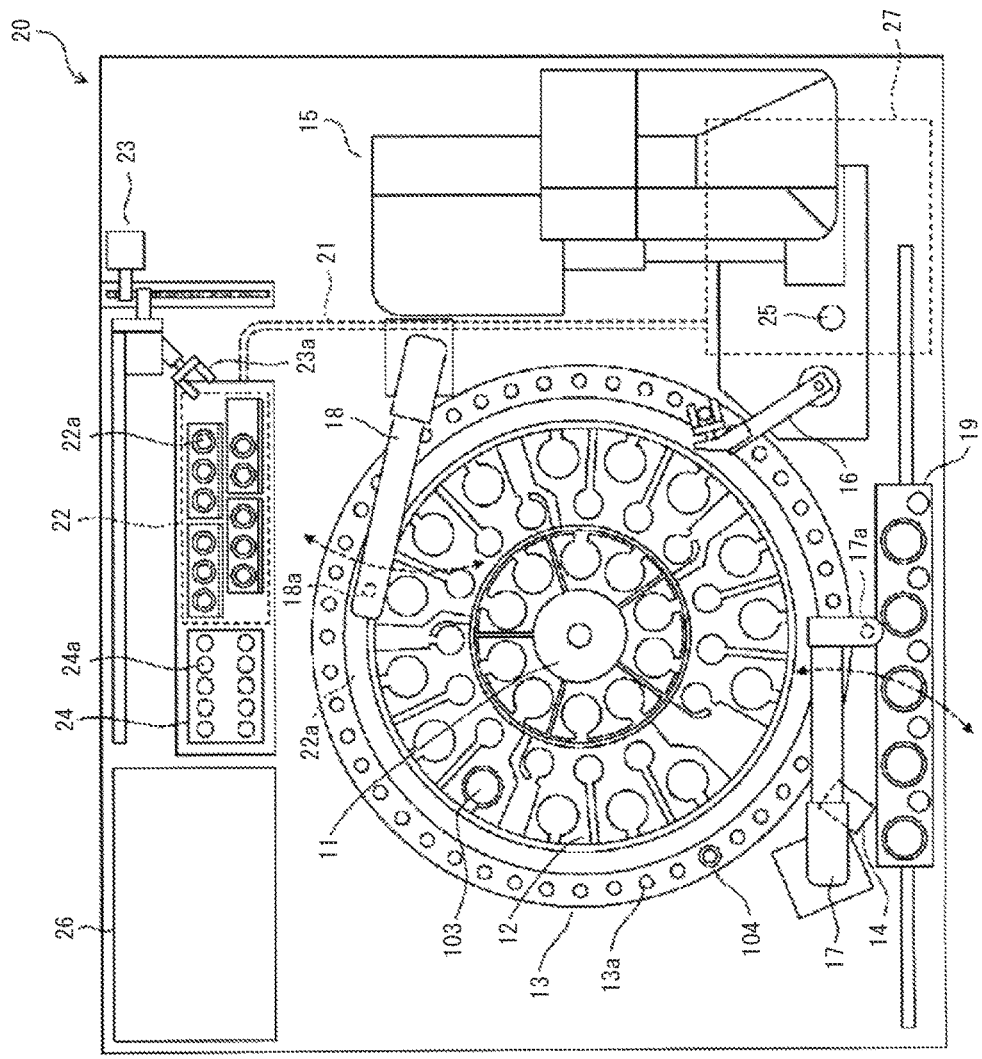
FIG. 3 is a plan view showing the inside of a measurement unit of the blood sample analyzer viewed from above.

The user can open the lid 2b to replace a lamp unit 27 (see FIG. 3). The user can open the cover 2c to replace a piercer 17a (see FIG. 3). The sample transport unit 30 transports a sample container 101 supported on a sample rack 102, to an aspiration position for the piercer 17a. The sample container 101 is sealed with a cap 101a made of rubber.

When using the blood sample analyzer 10, the user first presses the power button 2d of the measurement unit 20 to activate the measurement unit 20, and presses a power button 439 of the control apparatus 40 to activate the control apparatus 40. Upon activation of the control apparatus 40, a log-on screen is displayed on a display unit 41. The user inputs a use name and a password on the log-on screen to log on the control apparatus 40, and starts using the blood sample analyzer 10.

A configuration of the measurement apparatus will be described below. As shown in FIG. 3, the measurement unit 20 includes the reagent tables 11 and 12, a cuvette table 13, a bar code reader 14, a cuvette supply unit 15, a catcher 16, a sample dispensing arm 17, a reagent dispensing arm 18, an urgent sample setting part 19, an optical fiber 21 a detection unit 22, a cuvette transfer unit 23, a heating unit 24, a discard hole 25, a fluid unit 26, and the lamp unit 27.

(Measurement Specimen Preparation Section)

Each of the reagent tables 11 and 12 and the cuvette table 13 has an annular shape and is rotatable. The reagent tables 11 and 12 correspond to a reagent storage part, and reagent containers 103 are placed thereon. The bar code of each reagent container 103 placed on the reagent tables 11 and 12 is read by the bar code reader 14. Information (the kind of the reagent and the reagent ID) read from the bar code is inputted to the control apparatus 40, to be stored in a hard disk 434 (see FIG. 8). On the reagent table 11 and/or 12, a reagent container 103 containing a normal blood sample for preparation of a mixed sample may be placed.

The cuvette table 13 has support parts 13a formed therein which are a plurality of holes capable of supporting cuvettes 104 therein. New cuvettes 104 loaded by the user into the cuvette supply unit 15 are sequentially transferred by the cuvette supply unit 15, to be set in the support parts 13a of the cuvette table 13 by the catcher 16.

Stepping motors are respectively connected to the sample dispensing arm 17 and the reagent dispensing arm 18 so that the sample dispensing arm 17 and the reagent dispensing arm 18 can move in up-down directions and rotate. At the tip of the sample dispensing arm 17, the piercer 17a is provided whose tip is formed sharp so as to be able to puncture the cap 101a of each sample container 101. At the tip of the reagent dispensing arm 18, a pipette 18a is provided. Different from the piercer 17a, the tip of the pipette 18a is formed flat. A liquid surface detection sensor 213 of a capacitance type (see FIG. 4) is connected to the pipette 18a.

When a sample container 101 has been transported to a predetermined position by the sample transport unit 30 (see FIG. 2), the piercer 17a is positioned immediately above the sample container 101 by rotation of the sample dispensing arm 17. Then, the sample dispensing arm 17 is moved downwardly, the piercer 17a pierces the cap 101a of the sample container 101, and then, the blood sample contained in the sample container 101 is aspirated by the piercer 17a. In the case where an urgent blood sample is set in the urgent sample setting part 19, the piercer 17a aspirates the urgent blood sample by interrupting the samples supplied from the sample transport unit 30. The blood sample aspirated by the piercer 17a is discharged into an empty cuvette 104 on the cuvette table 13.

The cuvette 104 into which the blood sample has been discharged is transferred by a catcher 23a of the cuvette transfer unit 23, from the support part 13a in the cuvette table 13 to a support part 24a in the heating unit 24. The heating unit 24 heats the blood sample contained in the cuvette 104 set in the support part 24a to a predetermined temperature (for example, 37° C.) for a certain time period. When the heating of the blood sample by the heating unit 24 ends, this cuvette 104 is gripped by the catcher 23a again. Then, the cuvette 104 is located at a predetermined position while being gripped by the catcher 23a. In this state, the reagent aspirated by the pipette 18a is discharged into the cuvette 104.

For the dispensing of the reagent by the pipette 18a, first, the reagent tables 11 and 12 are rotated. Then, a reagent container 103 which contains the reagent corresponding to the measurement item is transported to the aspiration position for the pipette 18a. Then, after the pipette 18a has been located at the origin position in the up-down direction according to a sensor for detecting the origin position, the pipette 18a is lowered until the liquid surface detection sensor 213 detects that the lower end of the pipette 18a has come into contact with the liquid surface of the reagent. When the lower end of the pipette 18a has come into contact with the liquid surface of the reagent, the pipette 18a is further lowered to an extent that allows aspiration of the reagent by a necessary amount. Then, the lowering of the pipette 18a is stopped, and the reagent is aspirated by the pipette 18a. The reagent aspirated by the pipette 18a is discharged into the cuvette 104 gripped by the catcher 23a. Then, by the vibration function of the catcher 23a, the blood sample and the reagent in the cuvette 104 are stirred. Accordingly, a measurement specimen is prepared. Then, the cuvette 104 containing the measurement specimen is transferred by the catcher 23a to a support part 22a in the detection unit 22.

(Optical Information Obtainment Section)

The lamp unit 27 supplies light having a plurality of wavelengths to be used in detection of optical signals performed by the detection unit 22. With reference to FIG. 5, one example of the configuration of the lamp unit 27 will be described. The lamp unit 27 corresponds to a light source. The lamp unit 27 includes a halogen lamp 27a, a lamp case 27b, condensing lenses 27c to 27e, a disk-shaped filter part 27f, a motor 27g, a light-transmission-type sensor 27h, and an optical fiber coupler 27i.

Light from the lamp unit 27 is supplied to the detection unit 22 via the optical fiber 21. The detection unit 22 is provided with a plurality of support parts 22a each having a hole shape. A cuvette 104 can be inserted into each support part 22a. To each support part 22a, an end portion of the optical fiber 21 is attached. Accordingly, light from the optical fiber 21 can be emitted to the cuvette 104 supported in the support part 22a. The detection unit 22 emits, to the cuvette 104, light supplied from the lamp unit 27 via the optical fiber 21. The detection unit 22 detects the amount of light that has passed through the cuvette 104 (or the amount of scattered light from the cuvette 104).

Figure 6A:
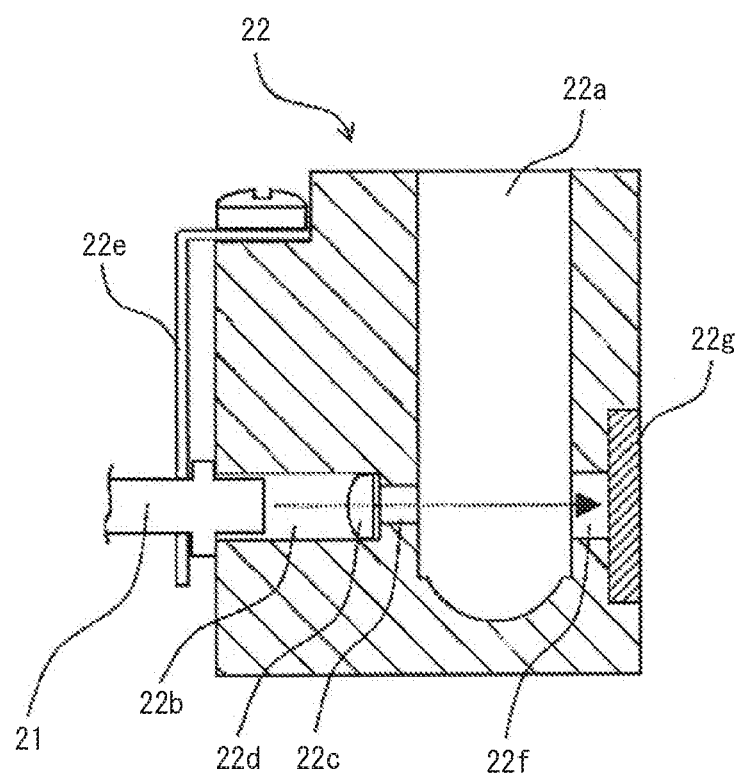
FIG. 6A shows a configuration of a detection unit provided in the measurement apparatus.

Each of FIGS. 6A to 6D shows an example of the configuration of one of the plurality of support parts 22a provided in the detection unit 22. However, the other support parts 22a each have the same configuration. With reference to FIG. 6A, a circular hole 22b into which the tip of the optical fiber 21 is to be inserted is formed in the detection unit 22. Further, a circular communication hole 22c which allows the hole 22b to communicate with the support part 22a is formed in the detection unit 22. The diameter of the hole 22b is greater than the diameter of the communication hole 22c. A lens 22d which collects light from the optical fiber 21 is disposed at an end of the hole 22b. Further, a hole 22f is formed in the inner wall of the support part 22a, at a position opposed to the communication hole 22c. A light detector 22g is disposed behind this hole 22f. The light detector 22g corresponds to a light receiver, and outputs an electric signal in accordance with the amount of received light. Light that has passed through the lens 22d is collected on the light receiving surface of the light detector 22g, via the communication hole 22c, the support part 22a, and the hole 22f. The optical fiber 21, with the end portion inserted in the hole 22b, is prevented from slipping off by a plate spring 22e.

Figure 6B:
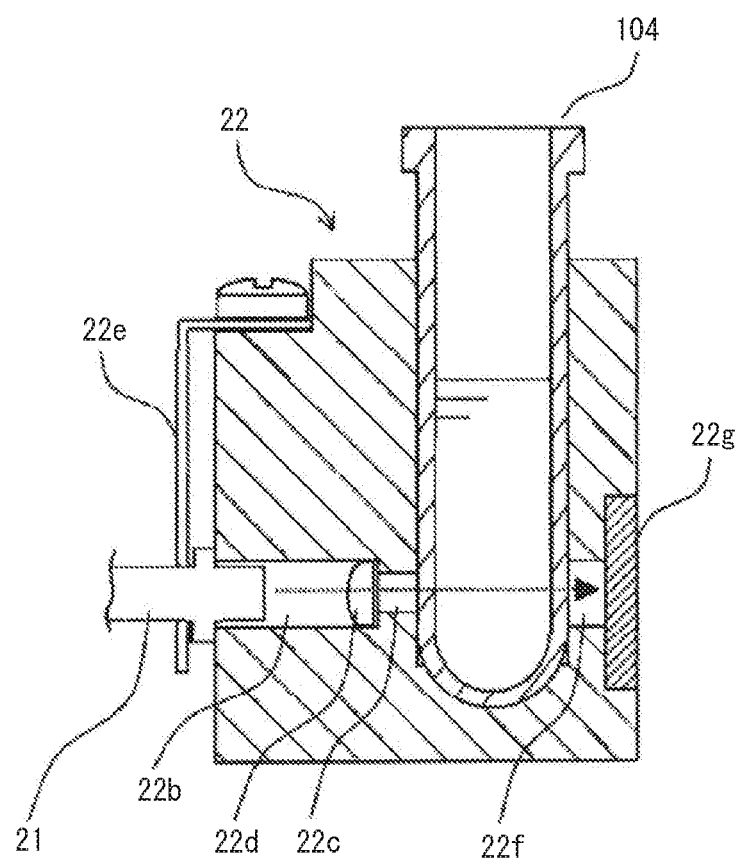
FIG. 6B shows a configuration of the detection unit provided in the measurement apparatus.

With reference to FIG. 6B, when the cuvette 104 is supported in the support part 22a, the light collected by the lens 22d passes through the cuvette 104 and the specimen contained in the cuvette 104, to be incident on the light detector 22g. When blood coagulation reaction advances in the specimen, the turbidity of the specimen increases accordingly. Associated with this, the amount of light (the amount of transmitted light) passing through the specimen decreases, and the level of the detection signal of the light detector 22g is lowered.

Figure 6C:
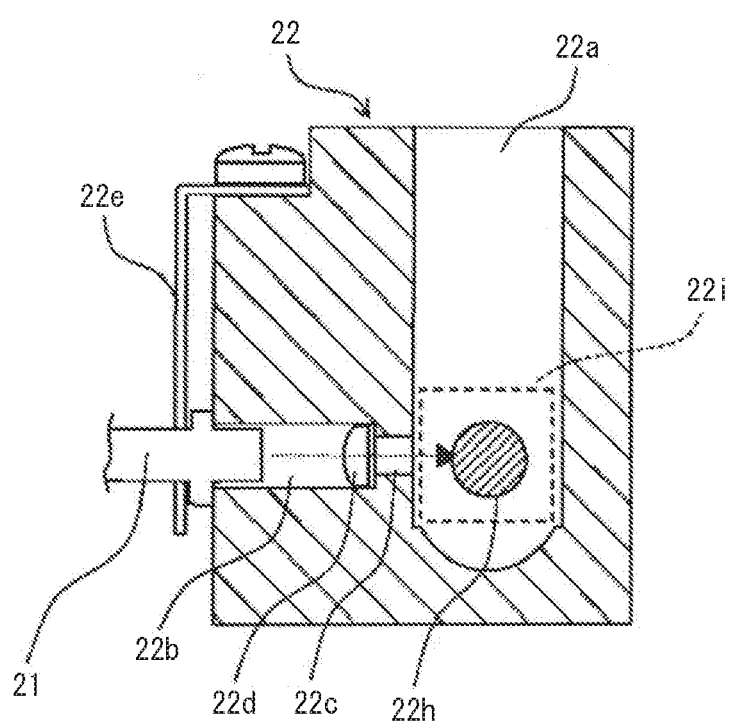
FIG. 6C shows a configuration of the detection unit provided in the measurement apparatus.
Figure 6D:
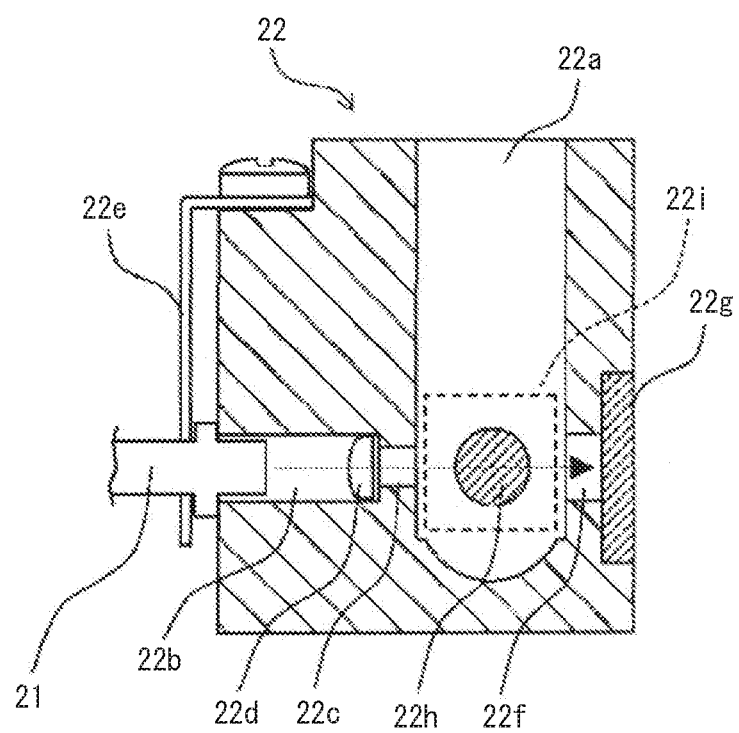
FIG. 6D shows a configuration of the detection unit provided in the measurement apparatus.

With reference to FIG. 6C, a configuration of the detection unit 22 when scattered light is used will be described. A hole 22h is provided in the inner side-surface of the support part 22a, at a position at the same height as the communication hole 22c. A light detector 22i is disposed behind this hole 22h. When a cuvette 104 is inserted in the support part 22a and light is emitted from the optical fiber 21, light scattered at the measurement specimen in the cuvette 104 is received by the light detector 22i via the hole 22h. In this example, the detection signal from the light detector 22i represents intensity of the scattered light from the measurement specimen. As shown in FIG. 6D, both of transmitted light that has passed through the measurement specimen and scattered light that has been scattered at the measurement specimen may be detected.

As described above, the detection unit 22 emits, to the cuvette 104, light supplied from the lamp unit 27, and obtains optical information from the measurement specimen. The obtained optical information is transmitted to the control apparatus 40. The control apparatus 40 performs analysis on the basis of the optical information, and displays the analysis result on the display unit 41.

After the measurement ends, the cuvette 104 that is no more needed is transported by the cuvette table 13, to be discarded into the discard hole 25 by the catcher 16. It should be noted that during the measurement operation, the piercer 17a and the pipette 18a are each cleaned as appropriate by a liquid such as a cleaning liquid supplied from the fluid unit 26.

Figure 4:
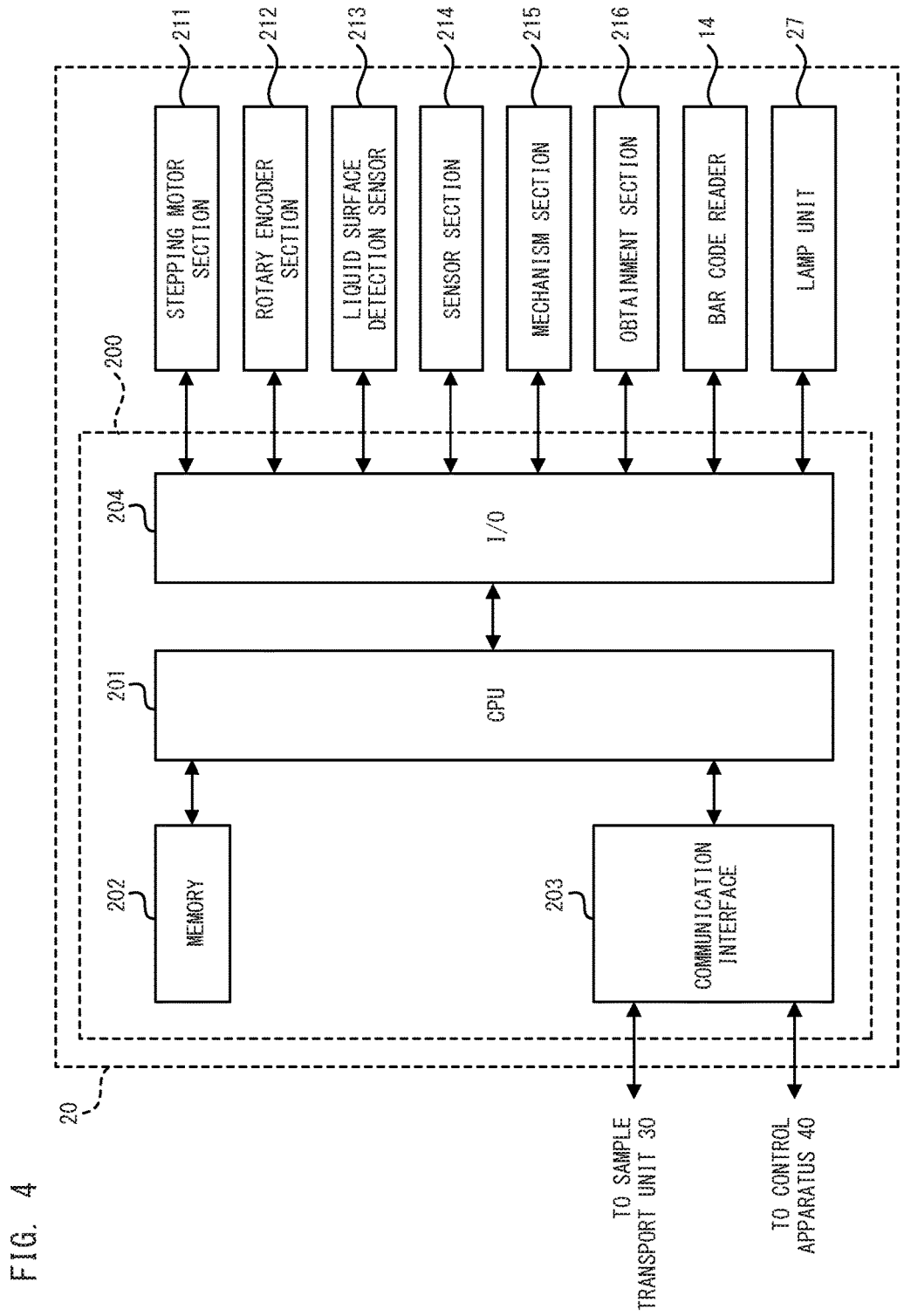
FIG. 4 shows a configuration of the measurement unit of the blood sample analyzer.

A hardware configuration of the measurement apparatus will be described below. As shown in FIG. 4, the measurement unit 20 includes a control section 200, a stepping motor section 211, a rotary encoder section 212, the liquid surface detection sensor 213, a sensor section 214, a mechanism section 215, an obtainment section 216, the bar code reader 14, and the lamp unit 27.

The control section 200 includes a CPU 201, a memory 202, a communication interface 203, and an I/O interface 204. The CPU 201 executes computer programs stored in the memory 202. The memory 202 is composed of a ROM, a RAM, a hard disk, and the like. The CPU 201 drives the sample transport unit 30 via the communication interface 203. The CPU 201 transmits/receives instruction signals and data to/from the control apparatus 40. The CPU 201 controls components in the measurement unit 20 via the I/O interface 204, and receives signals outputted from the components.

The stepping motor section 211 includes stepping motors for respectively driving the reagent tables 11 and 12, the cuvette table 13, the catcher 16, the sample dispensing arm 17, the reagent dispensing arm 18, and the cuvette transfer unit 23. The rotary encoder section 212 includes rotary encoders which output pulse signals in accordance with the amounts of rotational displacements of the respective stepping motors included in the stepping motor section 211.

The liquid surface detection sensor 213 is connected to the pipette 18a provided at the tip of the reagent dispensing arm 18. The liquid surface detection sensor 213 detects that the lower end of the pipette 18a has come into contact with the liquid surface of the reagent. The sensor section 214 includes a sensor for detecting that the pipette 18a has been located at the origin position in the up-down direction, and a sensor for detecting that the power button 2d has been pressed. The mechanism section 215 includes: mechanisms for driving the cuvette supply unit 15, the urgent sample setting part 19, the heating unit 24, and the fluid unit 26; and pneumatic sources which supply pressure to the piercer 17a and the pipette 18a so that the piercer 17a and the pipette 18a can perform dispensing operations. The obtainment section 216 includes the detection unit 22.

A configuration of the control apparatus 40 will be described below. As shown in FIG. 2, the control apparatus 40 is composed of the display unit 41, an input unit 42, and a computer body 43. The control apparatus 40 receives optical information from the measurement unit 20. The processor of the control apparatus 40 calculates parameters regarding derivative of clot waveform on the basis of optical information. The processor of the control apparatus 40 may calculate clotting time on the basis of optical information. Then, the processor of the control apparatus 40 executes a computer program for performing blood sample determination. Thus, the control apparatus 40 also functions as an apparatus for performing blood sample determination.

Figure 7:
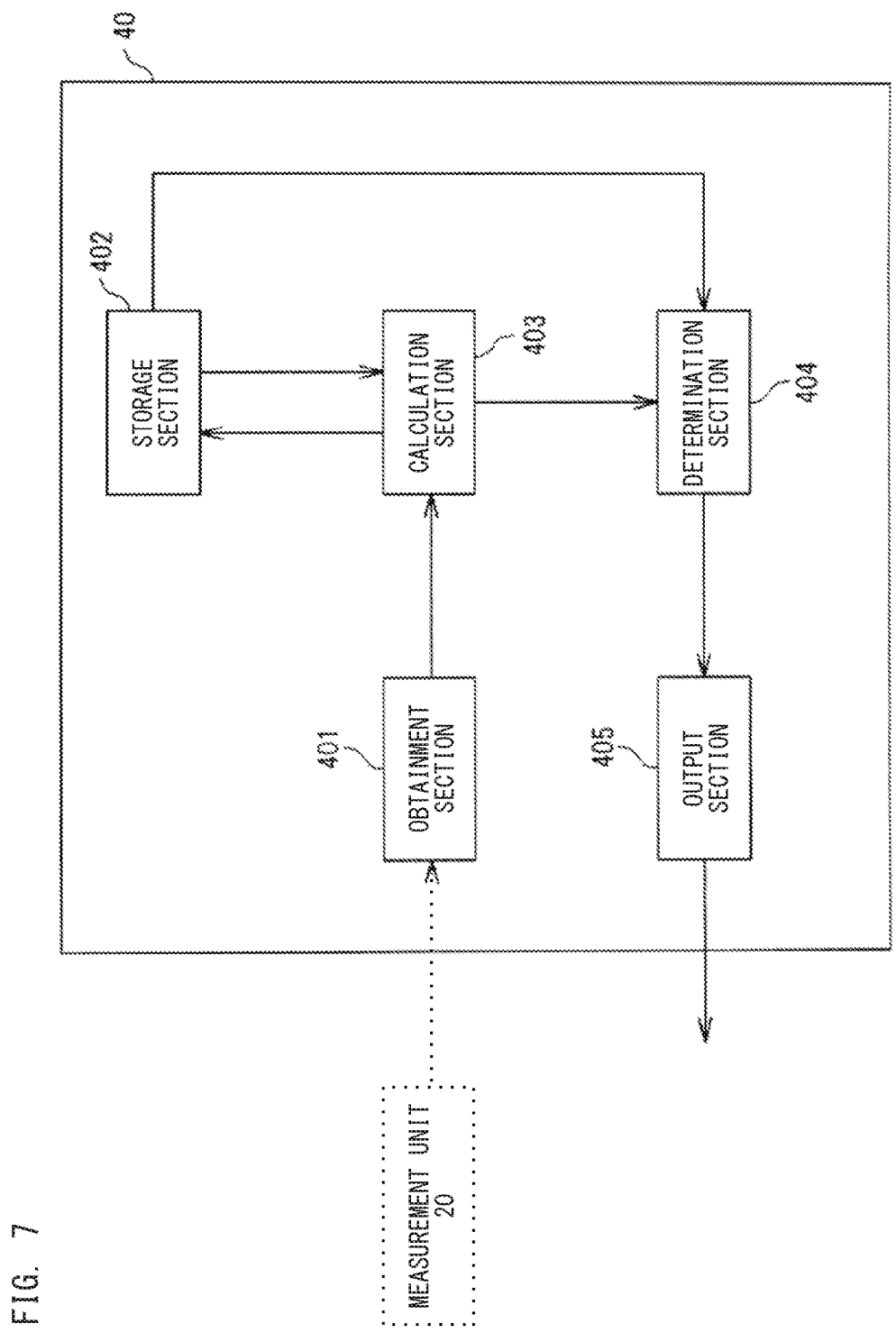
FIG. 7 shows a functional configuration of a control apparatus of the blood sample analyzer.

With respect to a functional configuration of the control apparatus 40, as shown in FIG. 7, the control apparatus 40 includes an obtainment section 401, a storage section 402, a calculation section 403, a determination section 404, and an output section 405. The obtainment section 401 is communicably connected to the measurement unit 20 via a network. The output section 405 is communicably connected to the display unit 41.

The obtainment section 401 obtains optical information transmitted from the measurement unit 20. The storage section 402 has stored therein equations for calculating values of various types of parameters regarding derivative of clot waveform, predetermined thresholds necessary for determination, and the like. The storage section 402 may also have stored therein equations for calculating clotting time, and a predetermined clotting time (for example, a reference value or a normal value of clotting time). The calculation section 403 calculates values of various types of parameters, in accordance with the equations stored in the storage section 402, by using the information obtained by the obtainment section 401. The determination section 404 determines whether the values of the parameters calculated by the calculation section 403 are smaller than their corresponding predetermined thresholds stored in the storage section 402. The output section 405 outputs the result of the determination made by the determination section 404, as reference information regarding the blood sample.

Figure 8:
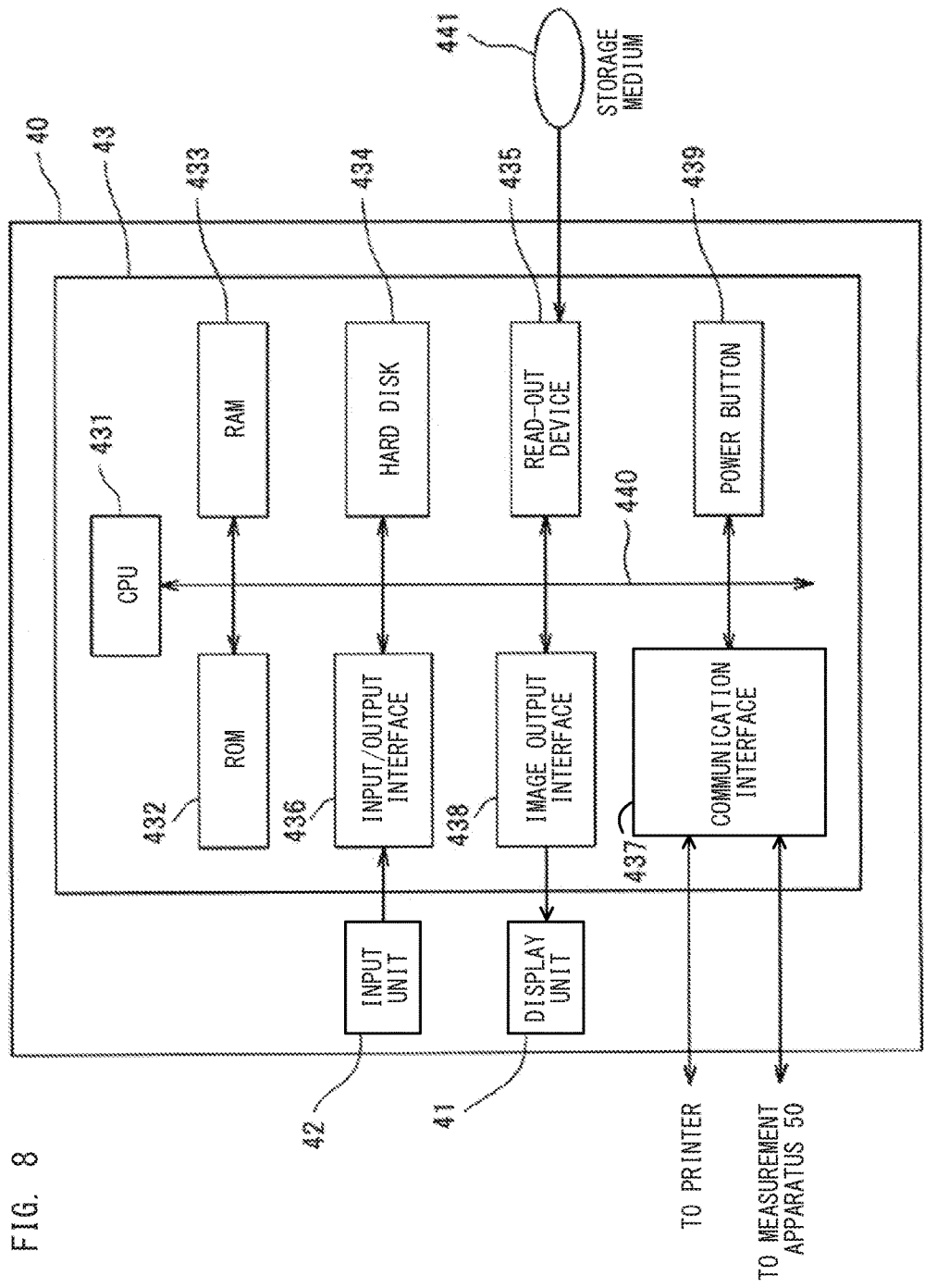
FIG. 8 shows a hardware configuration of the control apparatus of the blood sample analyzer.

As shown in FIG. 8, the computer body 43 of the control apparatus 40 includes a control section, the hard disk 434, a read-out device 435, an input/output interface 436, a communication interface 437 an image output interface 438, and the power button 439. The control section includes a CPU 431, a ROM 432, and a RAM 433. The CPU 431, the ROM 432, the RAM 433, the hard disk 434, the read-out device 435, the input/output interface 436, the communication interface 437, the image output interface 438, and the power button 439 are communicably connected to one another by a bus 440.

The CPU 431 executes computer programs stored in the ROM 432 and computer programs loaded on the RAM 433. By the CPU 431 executing application programs, the function blocks described above are realized. Accordingly, the computer system functions as a terminal being a determination apparatus for performing blood sample determination.

The ROM 432 is implemented by a mask ROM, a PROM, an EPROM, an EEPROM, or the like. The ROM 432 has stored therein computer programs to be executed by the CPU 431, and data to be used therefor.

The RAM 433 is implemented by an SRAM, a DRAM, or the like. The RAM 433 is used for reading out computer programs stored in the ROM 432 and the hard disk 434. The RAM 433 is also used as a work area for the CPU 431 when the CPU 431 executes these computer programs.

The hard disk 434 has installed therein an operating system, computer programs such as an application program (computer program for blood sample determination) to be executed by the CPU 431, data to be used in execution of the computer programs, and the settings of the control apparatus 40.

The read-out device 435 is composed of a flexible disk drive, a CD-ROM drive, a DVD-ROM drive, and the like. The read-out device 435 can read out computer programs or data stored in a portable storage medium 441 such as a CD or a DVD.

The input/output interface 436 is composed of: for example, serial interfaces such as USB, IEEE1394, and RS-232C; parallel interfaces such as SCSI, IDE, and IEEE1284; and analog interfaces such as a D/A converter and an A/D converter. The input unit 42 such as a keyboard and a mouse is connected to the input/output interface 436. The user inputs an instruction via the input unit 42, and the input/output interface 436 receives a signal inputted via the input unit 42.

The communication interface 437 is, for example, an Ethernet (registered trademark) interface or the like. The control apparatus 40 can transmit print data to a printer via the communication interface 437. The communication interface 437 is connected to the measurement unit 20. The CPU 431 transmits/receives instruction signals and data to/from the measurement unit 20 via the communication interface 437.

The image output interface 438 is connected to the display unit 41 implemented by an LCD, a CRT, or the like. The image output interface 438 outputs an image signal in accordance with image data to the display unit 41. The display unit 41 displays an image on the basis of the image signal outputted from the image output interface 438.

With reference to FIG. 4, during measurement operation, the CPU 201 of the measurement unit 20 temporarily stores, in the memory 202, data (optical information) obtained by digitizing the detection signal outputted from the detection unit 22 (see FIG. 3). The storage area of the memory 202 is divided into areas so as to correspond to the respective support parts 22a. In each area, data (optical information) is sequentially stored which is obtained when light of a predetermined wavelength is emitted to a cuvette 104 supported in its corresponding support part 22a. Thus, data is sequentially stored in the memory 202 for a predetermined measurement time period. When the measurement time period has elapsed, the CPU 201 stops storing data into the memory 202. Then, the CPU 201 transmits the stored data to the control apparatus 40 via the communication interface 203. The control apparatus 40 processes the received data to conduct analysis, and displays the analysis result on the display unit 41.

Figure 9:
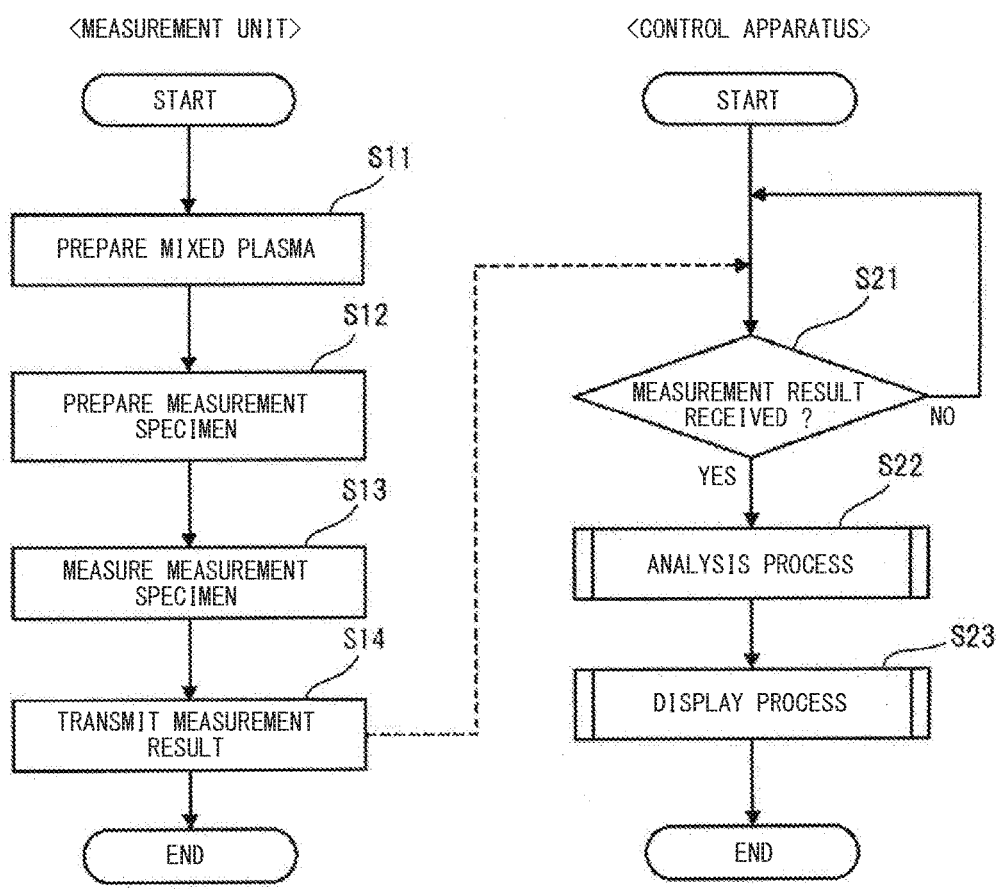
FIG. 9 is a flow chart showing a measurement process performed on a blood sample by the blood sample analyzer.

The processing in the measurement unit 20 is performed mainly under control of the CPU 201 of the measurement unit 20. The processing in the control apparatus 40 is performed mainly under control of the CPU 431 of the control apparatus 40. With reference to FIG. 9, upon start of a measurement process, the measurement unit 20 aspirates a normal plasma by a predetermined amount from a reagent container 103 containing the normal plasma, and dispenses the aspirated normal plasma into an empty cuvette 104. Then, the measurement unit 20 aspirates a subject plasma by a predetermined amount from a sample container 101 having been transported by the sample transport unit. The measurement unit 20 dispenses the aspirated subject plasma into the cuvette 104 in which the normal plasma has been dispensed, and stirs the mixture. Thereby, the measurement unit 20 prepares a mixed plasma (step S11). In the case where the subject plasma is also to be measured, the measurement unit 20 aspirates the subject plasma from the sample container 101, and dispenses the aspirated subject plasma into an empty cuvette 104 on the cuvette table 13. In the case where the normal plasma is also to be measured, the measurement unit 20 aspirates the normal plasma from a reagent container 103 that contains the normal plasma and that is held on the reagent storage part. The measurement unit 20 dispenses the aspirated normal plasma into an empty cuvette 104 on the cuvette table 13.

Next, the measurement unit 20 transfers, to the heating unit 24, the cuvette 104 into which the plasma has been dispensed. Then, the measurement unit 20 heats the plasma in the cuvette 104 to a predetermined temperature (for example, 37° C.). Then, the measurement unit 20 adds a reagent to the cuvette 104 to prepare a measurement specimen (step S12). The measurement unit 20 starts counting time from the time point of the addition of the reagent into the cuvette 104.

Then, the measurement unit 20 transfers, to the detection unit 22, the cuvette 104 into which the reagent has been added. Then, the measurement unit 20 emits light to the cuvette 104 to measure the measurement specimen (step S13). In this measurement, data based on light having a wavelength of 660 nm (the amount of scattered light or the amount of transmitted light) is sequentially stored in the memory 202 for the measurement time period. At this time, the data is stored in the memory 202, associated with the elapsed time from the reagent addition time point. When the measurement time period has elapsed, the measurement unit 20 stops the measurement, and transmits the measurement result (data) stored in the memory 202, to the control apparatus 40 (step S14). When the control apparatus 40 has received the measurement result (data) from the measurement unit 20 (step S21: YES), the control apparatus 40 executes an analysis process on the received measurement result (step S22). That is, with respect to the measurement specimen, the control apparatus 40 calculates parameters (|min 1|, |min 2|, and max 2) regarding derivative of clot waveform, and makes determination based on the parameters. It should be noted that the control apparatus 40 may calculate the clotting time and the clot waveform of the measurement specimen. Further, on the basis of the clotting time of the measurement specimen prepared from the subject plasma, the control apparatus 40 may determine whether prolongation of the clotting time of the subject plasma is observed. After performing the analysis process, the control apparatus 40 executes a display process of the analysis result (step S23).

Figure 10A:
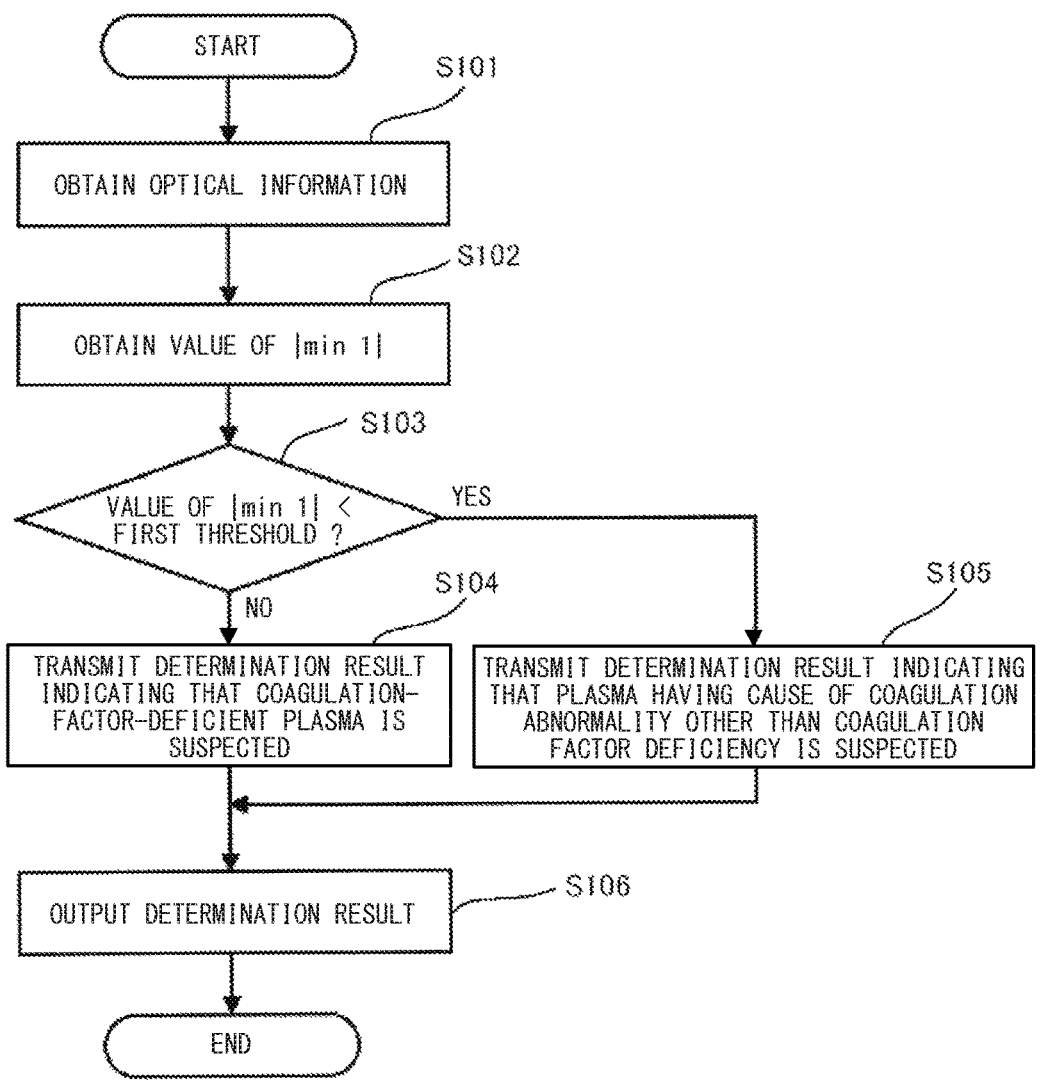
FIG. 10A is a flow chart showing an analysis process performed on a blood sample by the blood sample analyzer.

With reference to FIG. 10A, the flow of the process that uses one parameter regarding derivative of clot waveform will be described. Here, an example case will be described in which: on the basis of optical information regarding the amount of light obtained from a measurement specimen, the value of |min 1| is obtained as the value of the parameter regarding derivative of clot waveform; and the obtained value is compared with its corresponding predetermined threshold, thereby to make a blood sample determination. However, the present embodiment is not limited to this example only. In this example, instead of |min 1|, the value of |min 2| or max 2 may be obtained to make a determination.

First, in step S101, on the basis of the data (the amount of scattered light or the amount of transmitted light) received from the measurement unit 20, the obtainment section 401 of the control apparatus 40 obtains optical information (scattered light intensity, or transmittance or absorbance). Next, in step S102, from the optical information obtained by the obtainment section 401, the calculation section 403 calculates the value of |min 1| in accordance with an equation for calculating the parameter regarding derivative of clot waveform stored in the storage section 402. Preferably, the parameter is calculated from the optical information of one measurement specimen prepared from the mixed plasma. It should be noted that the clotting time and the clot waveform are not used in the process of determination described later. However, the calculation section 403 may further calculate the clotting time and the clot waveform from the optical information obtained by the obtainment section 401.

In step S103, by using the value of |min 1| calculated by the calculation section 403 and the first threshold stored in the storage section 402, the determination section 404 determines whether the subject plasma is suspected to be a coagulation-factor-deficient plasma. Here, when the value of |min 1| is not smaller than the first threshold (that is, the value of |min 1| is greater than or equal to the first threshold), the process is advanced to step S104. In step S104, the determination section 404 transmits, to the output section 405, a determination result indicating that the subject plasma is suspected to be a coagulation-factor-deficient plasma. On the other hand, when the value of |min 1| is smaller than the first threshold, the process is advanced to step S105. In step S105, the determination section 404 transmits, to the output section 405, a determination result indicating that the subject plasma is suspected to be a plasma having a cause of coagulation abnormality other than coagulation factor deficiency. It should be noted that in the case where the value of |min 2| is used, the value of |min 2| is compared with the second threshold, and in the case where the value of max 2 is used, the value of max 2 is compared with the third threshold.

In step S106, the output section 405 outputs the determination result to be displayed on the display unit 41 or printed by a printer. Alternatively, the output section 405 may output the determination result in sound. Accordingly, the determination result can be provided to the user as reference information regarding the subject plasma.

Figure 10B:
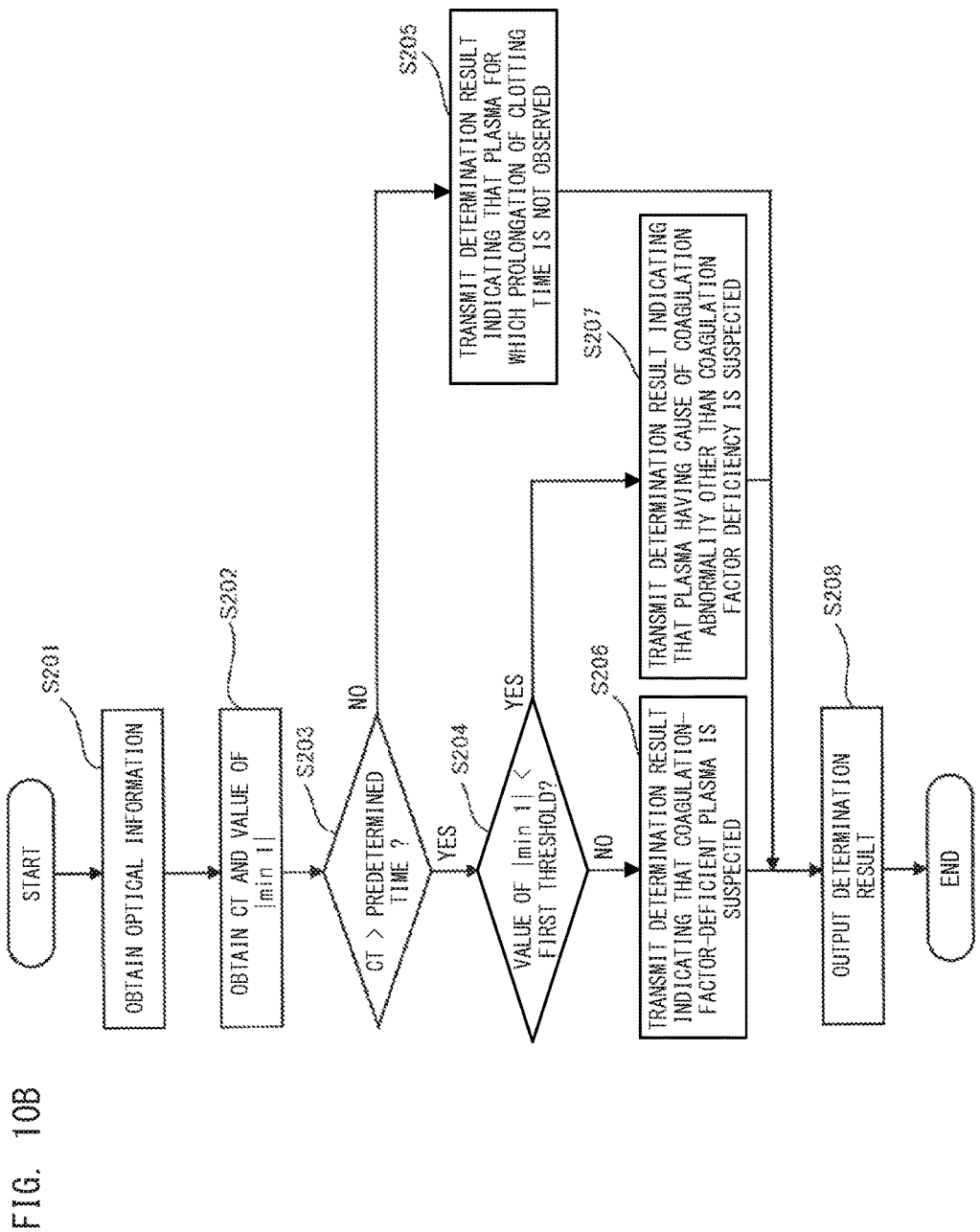
FIG. 10B is a flow chart showing an analysis process performed on a blood sample by the blood sample analyzer.

The flow of the process further including a step of comparing the clotting time of the subject plasma with a predetermined time will be described with reference to FIG. 10B. Here, an example case will be described in which: the clotting time is obtained from optical information regarding the amount of light from a measurement specimen (first measurement specimen) prepared from the subject plasma; and when the clotting time is longer than a predetermined time, the value of |min 1| obtained from optical information regarding the amount of light of a measurement specimen (second measurement specimen) prepared from the mixed plasma is compared with its corresponding predetermined threshold, thereby to make a determination on the subject plasma. However, the present embodiment is not limited to this example only. In this example, instead of |min 1|, the value of |min 2| or max 2 may be obtained to make a determination.

First, in step S201, on the basis of the data received from the measurement unit 20, the obtainment section 401 of the control apparatus 40 obtains optical information of the first and second measurement specimens. Next, in step S202, from the optical information of the first measurement specimen obtained by the obtainment section 401, the calculation section 403 calculates the clotting time (Clotting time: hereinafter, also referred to as "CT") of the subject plasma, in accordance with an equation for calculating the clotting time stored in the storage section 402. The calculation section 403 also calculates the value of |min 1| of the mixed plasma in accordance with an equation for calculating a parameter regarding derivative of clot waveform stored in the storage section 402, from optical information of the second measurement specimen obtained by the obtainment section 401. Preferably, the parameter is calculated from the optical information of one second measurement specimen prepared from the mixed plasma. The calculation section 403 may further calculate the clot waveform from the optical information obtained by the obtainment section 401.

In step S203, the determination section 404 compares the CT calculated by the calculation section 403 with a predetermined time. Here, the predetermined time may be a clotting time of a normal plasma stored in advance in the storage section 402, or may be a clotting time calculated by measuring the normal plasma in the same manner as in the case of the subject plasma. In step S203, when the CT is longer than the predetermined time, the process is advanced to step S204. On the other hand, when the CT is not loner than the predetermined time (that is, the CT is shorter than or equal to the predetermined time), the process is advanced to step S205. In step S205, the determination section 404 transmits, to the output section 405, a determination result indicating that the subject plasma is a plasma for which prolongation of the clotting time is not observed.

In step S204, the determination section 404 compares the value of |min 1| calculated by the calculation section 403 with the first threshold stored in the storage section 402. When the value of |min 1| is not smaller than the first threshold (that is, when the value of |min 1| is greater than or equal to the first threshold), the process is advanced to step S206. On the other hand, when the value of |min 1| is smaller than the first threshold, the process is advanced to step S207. Steps S206 and S207 are the same as steps S104 and S105 described above. Then, the determination section 404 transmits a determination result to the output section 405. Step S208 is the same as step S106 described above.

Figure 10C:
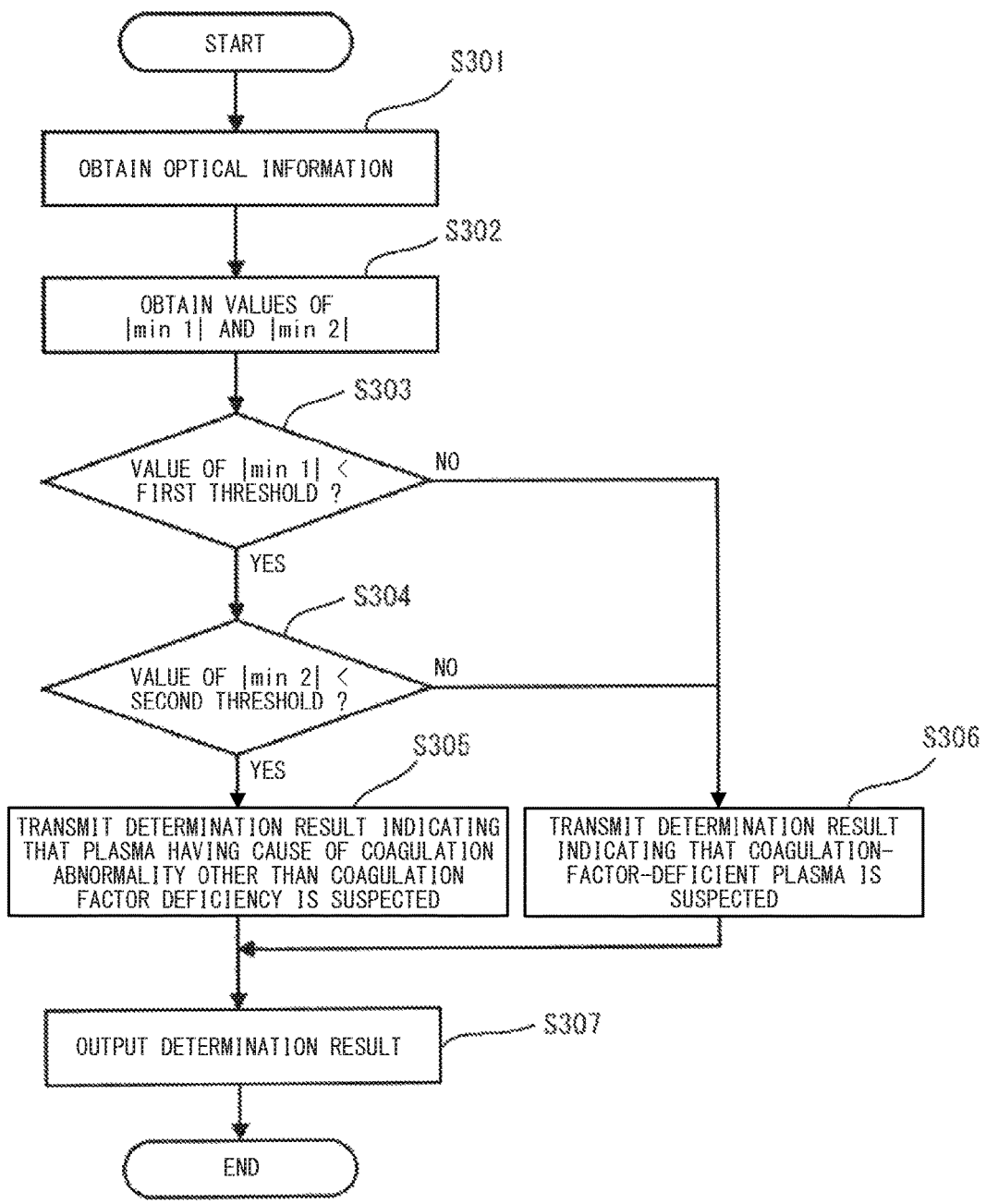
FIG. 10C is a flow chart showing an analysis process performed on a blood sample by the blood sample analyzer.

With reference to FIG. 10C, the flow of a process that uses two parameters regarding derivative of clot waveform will be described. Here, an example case will be described in which: on the basis of the optical information regarding the amount of light from a measurement specimen, the values of |min 1| and |min 2| are obtained; and the obtained values are compared with their corresponding predetermined thresholds, thereby to make a blood sample determination. However, the present embodiment is not limited to this example only. In this example, instead of either one of |min 1 and |min 2|, the value of max 2 may be obtained to make a determination. Alternatively, in this example, the process may further include a step of comparing the clotting time of the subject plasma with a predetermined time. Then, when the clotting time is longer than the predetermined time, the obtained values of the parameters may be compared with their corresponding predetermined thresholds, thereby to make a blood sample determination. When the clotting time is shorter than or equal to the predetermined time, a determination result may be outputted which indicates that the subject plasma is a sample for which prolongation of the clotting time is not observed.

First, in step S301, on the basis of the data received from the measurement unit 20, the obtainment section 401 of the control apparatus 40 obtains optical information. Next, in step S302, from the optical information obtained by the obtainment section 401, the calculation section 403 calculates the values of |min 1| and |min 2|, in accordance with equations for calculating the parameters regarding derivative of clot waveform stored in the storage section 402. The calculation section 403 may further calculate the clotting time and the clot waveform from the optical information obtained by the obtainment section 401.

In step S303, the determination section 404 compares the value of |min 1| calculated by the calculation section 403 with the first threshold stored in the storage section 402. When the value of |min 1| is smaller than the first threshold, the process is advanced to step S304. In step S304, the determination section 404 compares the value of |min 2| calculated by the calculation section 403 with the second threshold stored in the storage section 402. When the value of |min 2| is smaller than the second threshold, the process is advanced to step S305. In step S305, the determination section 404 transmits, to the output section 405, a determination result indicating that the subject plasma is suspected to be a plasma having a cause of coagulation abnormality other than coagulation factor deficiency.

On the other hand, in step S303, when the value of |min 1| is not smaller than the first threshold (that is, the value of |min 1| is greater than or equal to the first threshold), the process is advanced to step S306. In step S304, when the value of |min 2| is not smaller than the second threshold (that is, the value of |min 2| is greater than or equal to the second threshold), the process is advanced to step S306. In step S306, the determination section 404 transmits, to the output section 405, a determination result indicating that the subject plasma is suspected to be a coagulation-factor-deficient plasma. It should be noted that, in the present embodiment, the order of the processes of step S303 and step S304 may be switched with each other as desired. Step S307 is the same as step S106 described above.

Figure 10D:
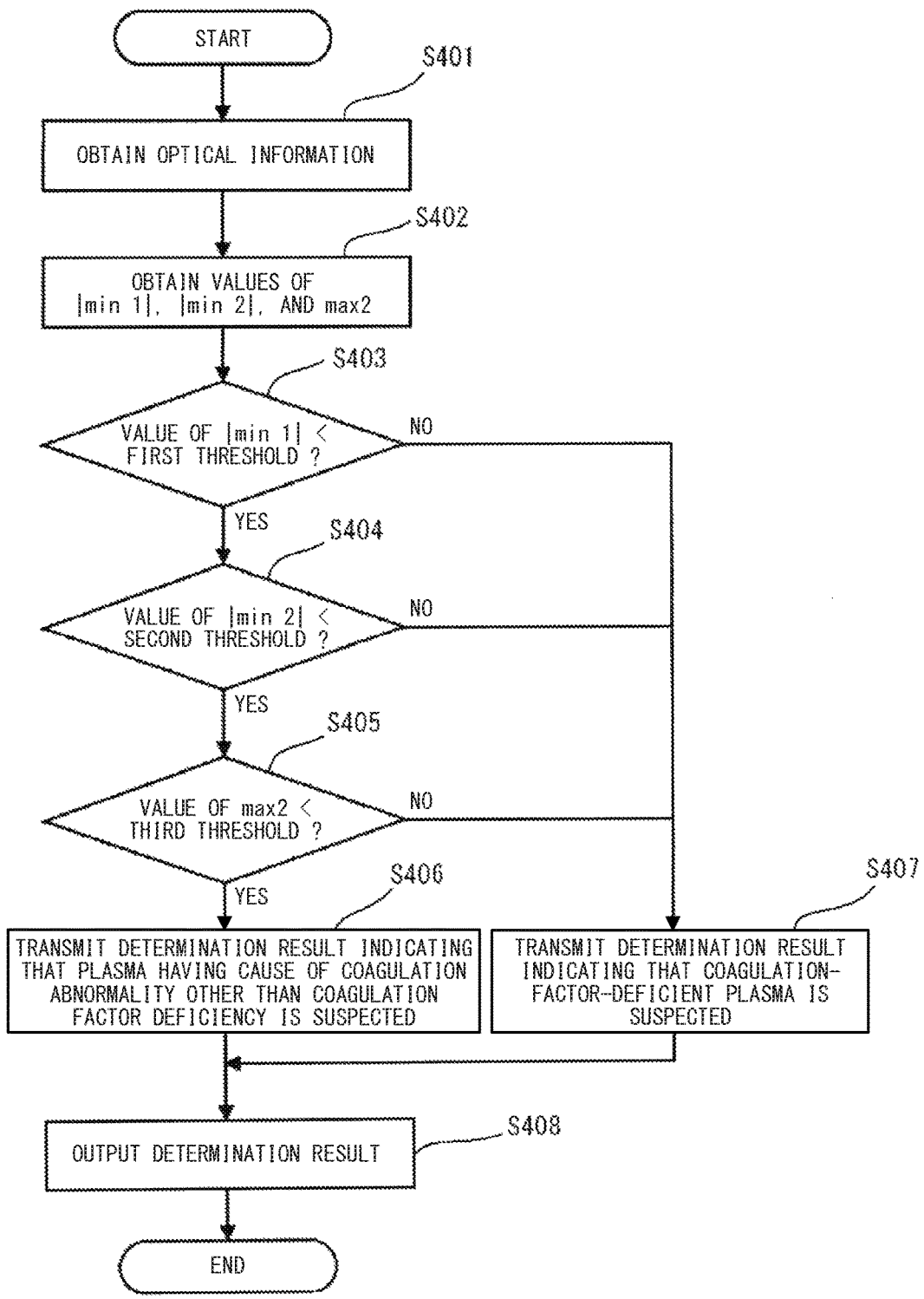
FIG. 10D is a flow chart showing an analysis process performed on a blood sample by the blood sample analyzer.

With reference to FIG. 10D, the flow of the process that uses three parameters regarding derivative of clot waveform will be described. Here, an example case will be described in which: on the basis of the optical information regarding the amount of light from the measurement specimen, the values of |min 1|, |min 2|, and max 2 are obtained; and the obtained values are compared with their corresponding predetermined thresholds, thereby to make a blood sample determination. However, the present embodiment is not limited to this example only. In this example, the process may further include a step of comparing the clotting time of the subject plasma with a predetermined time. Then, when the clotting time is longer than the predetermined time, the obtained values of the parameters may be compared with their corresponding predetermined thresholds, to make a blood sample determination. When the clotting time is shorter than or equal to the predetermined time, a determination result may be outputted which indicates that the subject plasma is a sample for which prolongation of the clotting time is not observed.

First, in step S401, on the basis of the data received from the measurement unit 20, the obtainment section 401 of the control apparatus 40 obtains optical information. Next, in step S402, from the optical information obtained by the obtainment section 401, the calculation section 403 calculates the values of |min 1|, |min 2|, and max 2 in accordance with equations for calculating parameters regarding derivative of clot waveform stored in the storage section 402. The calculation section 403 may further calculate the clotting time and the clot waveform from the optical information.

In step S403, the determination section 404 compares the value of |min 1| calculated by the calculation section 403 with the first threshold stored in the storage section 402. When the value of |min 1| is smaller than the first threshold, the process is advanced to step S404. In step S404, the determination section 404 compares the value of |min 2| calculated by the calculation section 403 with the second threshold stored in the storage section 402. When the value of |min 2| is smaller than the second threshold, the process is advanced to step S405. In step S405, the determination section 404 compares the value of max 2 calculated by the calculation section 403 with the third threshold stored in the storage section 402. When the value of max 2 is smaller than the third threshold, the process is advanced to step S406. In step S406, the determination section 404 transmits, to the output section 405, a determination result indicating that the subject plasma is suspected to be a plasma having a cause of coagulation abnormality other than coagulation factor deficiency.

On the other hand, in step S403, when the value of |min 1| is not smaller than the first threshold (that is, the value of |min 1| is greater than or equal to the first threshold), the process is advanced to step S407. In step S404, when the value of |min 2| is not smaller than the second threshold (that is, the value of |min 2| is greater than or equal to the second threshold), the process is advanced to step S407. In step S405, when the value of max 2 is not smaller than the third threshold (that is, the value of max 2 is greater than or equal to the third threshold), the process is advanced to step S407.

In step S407, the determination section 404 transmits, to the output section 405, a determination result indicating that the subject plasma is suspected to be a coagulation-factor-deficient plasma. It should be noted that, in the present embodiment, the order of the processes of step S403, step S404, and step S405 may be changed with one another as desired. Step S408 is the same as step S106 described above.

Figure 10E:
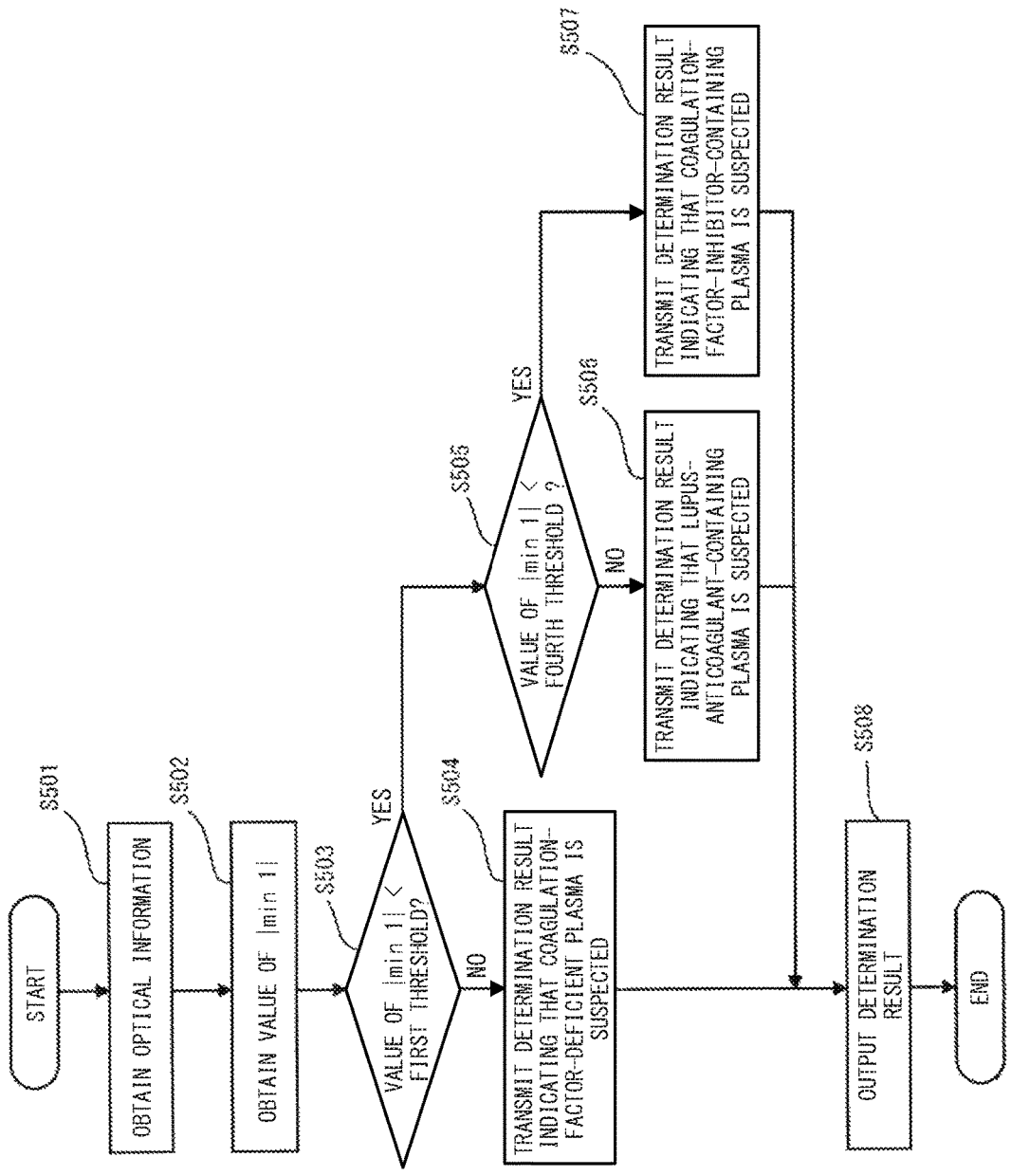
FIG. 10E is a flow chart showing an analysis process performed on a blood sample by the blood sample analyzer.

With reference to FIG. 10E, the flow of the process that further determines, when it has been determined that the subject plasma is suspected to be a plasma having a cause of coagulation abnormality other than coagulation factor deficiency, whether the subject plasma is suspected to be a plasma containing LA or is suspected to be a plasma containing a coagulation factor inhibitor, on the basis of the obtained value of a parameter, will be described. Here, an example case will be described in which: when the value of |min 1| is smaller than the first threshold, the value of |min 1| is further compared with the fourth threshold; and on the basis of the result of the comparison, whether the subject plasma is suspected to be a plasma containing LA or suspected to be a plasma containing a coagulation factor inhibitor is determined. However, the present embodiment is not limited to this example only. In this example, instead of |min 1|, the value of |min 2| or max 2 may be obtained to make a determination. Alternatively, a blood sample determination may be made by using a plurality of parameters. Still alternatively, the process may further include a step of comparing the clotting time of the subject plasma with a predetermined time, and when the clotting time is longer than the predetermined time, the obtained value of the parameter is compared with its corresponding predetermined threshold, thereby to make a blood sample determination. When the clotting time is shorter than or equal to the predetermined time, a determination result may be outputted which indicates that the subject plasma is a sample for which prolongation of the clotting time is not observed.

Steps S501 to S504 shown in FIG. 10E are the same as steps S101 to S104 shown in FIG. 10A. In step S503, when the value of |min 1| is smaller than the first threshold, the process is advanced to step S505. In step S505, by using the value of |min 1| and the fourth threshold stored in the storage section 402, the determination section 404 determines whether the subject plasma is suspected to be a plasma containing LA or is suspected to be a plasma containing a coagulation factor inhibitor. When the value of |min 1| is not smaller than the fourth threshold (that is, the value of |min 1| is greater than or equal to the fourth threshold), the process is advanced to step S506. In step S506, the determination section 404 transmits, to the output section 405, a determination result indicating that the subject plasma is suspected to be a plasma containing LA. On the other hand, when the value of |min 1| is smaller than the fourth threshold, the process is advanced to step S507. In step S507, the determination section 404 transmits, to the output section 405, a determination result indicating that the subject plasma is suspected to be a plasma containing a coagulation factor inhibitor. It should be noted that, when the value of |min 2| is used, the value of |min 2| is compared with the fifth threshold, and when the value of max 2 is used, the value of max 2 is compared with the sixth threshold. Step S508 is the same as step S106 described above.

Figure 11:
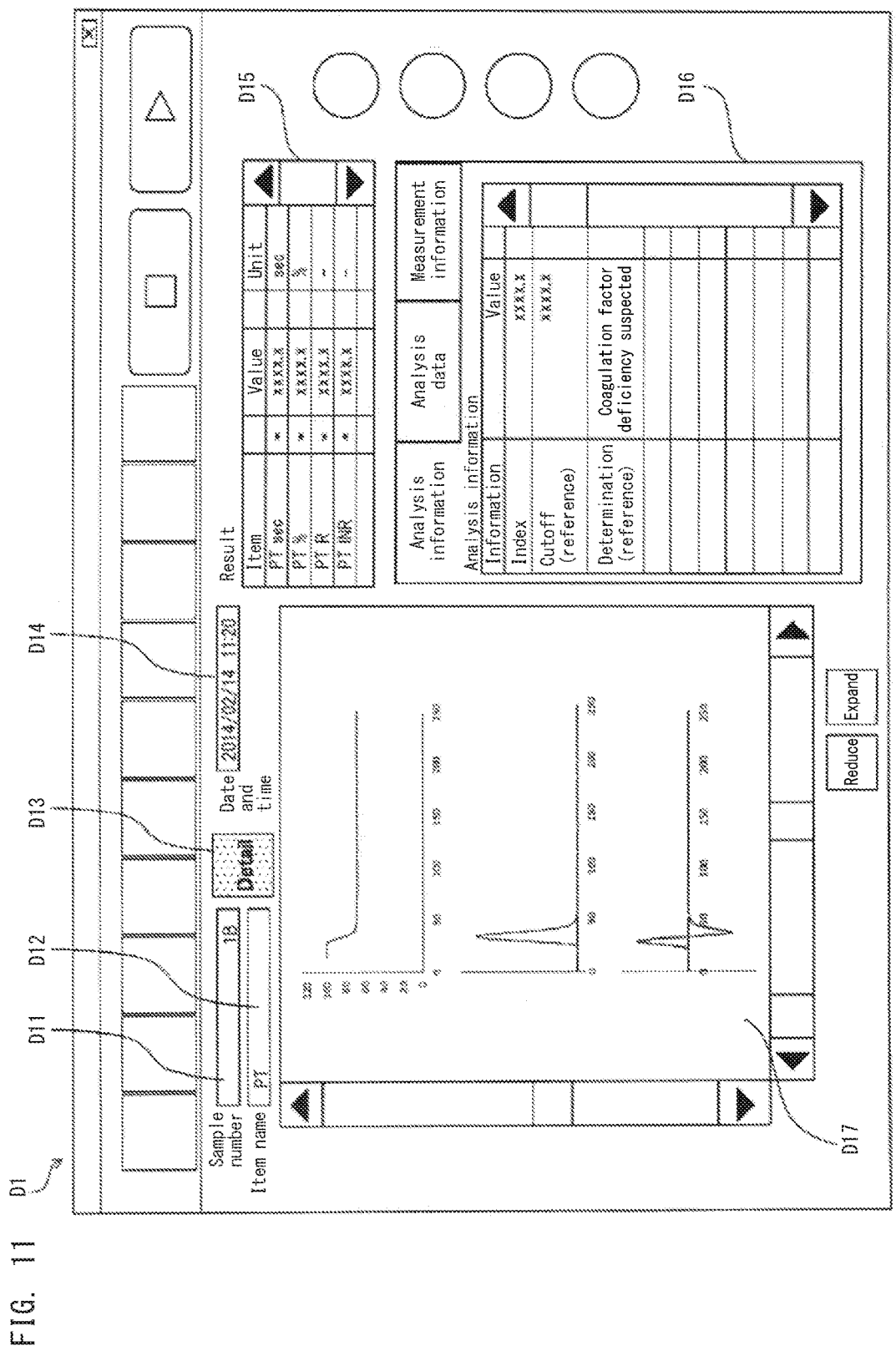
FIG. 11 shows one example of a screen on which to display an analysis result obtained by the blood sample analyzer.

As one example of a screen on which to display the analysis result, a screen having displayed thereon a result of analysis performed on the coagulation process of a mixed plasma by use of a prothrombin time measuring reagent will be described with reference to FIG. 11. A screen D1 includes a region D11 for displaying a sample number, a region D12 for displaying a measurement item name, a button D13 for displaying a detailed screen, a region D14 for displaying measurement date and time, a region D15 for displaying a measurement result, a region D16 for displaying analysis information, and a region D17 for displaying a clot waveform and graphs obtained by calculating the derivative of the clot waveform.

In the region D15, measurement items and measurement values are displayed. In the region D15, "PT sec" is prothrombin time. In addition to the prothrombin time (PT sec), values (PT %, PT R, PT INR) which are predetermined parameter values converted from the prothrombin time may be displayed in the region DIS.

In the region D16, analysis items and reference information are displayed. In the region D16, "Index" is the value of the parameter regarding derivative of clot waveform used in the determination. "Cutoff (reference)" is a predetermined threshold that corresponds to the parameter value used in the determination. "Determination (reference)" is the determination result obtained by the blood sample analyzer, and indicates that the subject plasma is suspected to be a coagulation-factor-deficient plasma. It is desirable that disease diagnosis is performed in consideration of not only this determination result but also information such as other test results. Therefore, in order to show that the predetermined thresholds and the determination result by the blood sample analyzer according to the present embodiment are reference information, the word "(reference)" is shown. In FIG. 11, the determination result is displayed in characters "Coagulation factor deficiency suspected", but the determination result may be indicated by means of a figure or a symbol such as a flag. Alternatively, the determination result may be outputted in sound.

Examples will be described in detail below, but the above embodiments are not limited to these Examples.

EXAMPLE

Example 1

It was examined whether coagulation-factor-deficient samples, LA positive samples, and coagulation-factor-inhibitor positive samples can be distinguished from one another, on the basis of the parameters regarding derivative of clot waveform.

(1) Reagent

As the clotting time measuring reagent, Thrombocheck APTT-SL A (Sysmex Corporation) being an APTT reagent and Thrombocheck 20 mM calcium chloride solution (Sysmex Corporation) were used. As the normal plasma, CRYOcheck Pooled Normal Plasma (Precision BioLogic Inc.) which is a normal plasma for cross-mixing test was used. As the control specimen for quality control, COAGTROL IX and COAGTROL IIX (Sysmex Corporation) were used.

(2) Subject Plasma

As the subject plasma, plasmas of factor V deficient patients (3 cases), plasmas of factor VIII deficient patients (4 cases), plasmas of LA positive patients (8 cases), and plasmas of coagulation factor VIII inhibitor positive patients (5 cases) were used.

(3) Measurement

For preparation and measurement of specimens, a fully automatic blood coagulation measurement apparatus CS-2400 (Sysmex Corporation) was used. Each subject plasma and the normal plasma above were mixed at a proportion of 5:5, and the mixture was dispensed into a reaction cuvette to make a mixed plasma having a total volume of 50 µL in which the ratio of subject plasma is 50% (v/v). Then, the mixed plasma was heated at 37° C. for 1 minute. To this reaction cuvette, the above-mentioned APTT reagent (50 µL) heated at 37° C. in advance was added, and the mixture was caused to react at 37° C. for 3 minutes. Then, the 20 mM calcium chloride solution (50 µL) was added to the mixture, and the transmittance was continuously measured for 420 seconds. The normal plasma was also measured in the same manner.

(4) Analysis Result

On the basis of the temporal change of the obtained transmittance, |min 1|, |min 2|, and max 2 were calculated as the parameters regarding derivative of clot waveform. The proportions (%) of |min 1|, |min 2, and max 2 of each subject plasma relative to the values of |min 1|, |min 2|, and max 2 of the normal plasma were calculated and plotted on graphs. The obtained graphs are shown in FIGS. 12A to 12C.

Figure 12A:
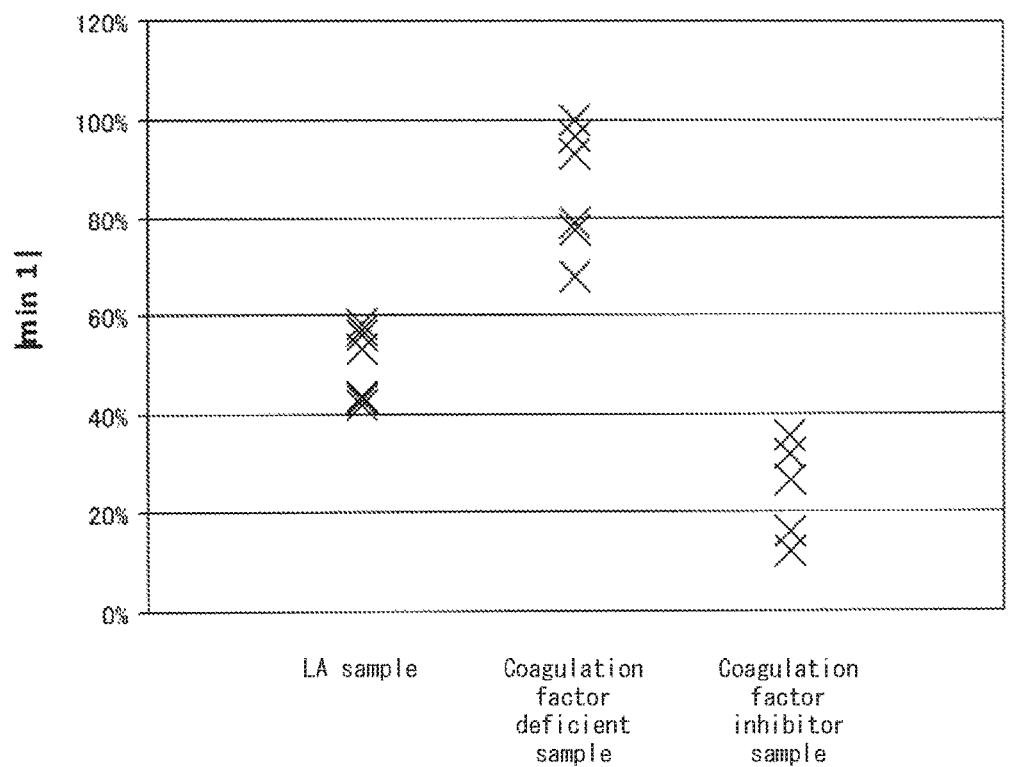
FIG. 12A is a graph showing the proportion of |min 1| of each subject plasma relative to the value of |min 1| of a normal plasma.
Figure 12B:
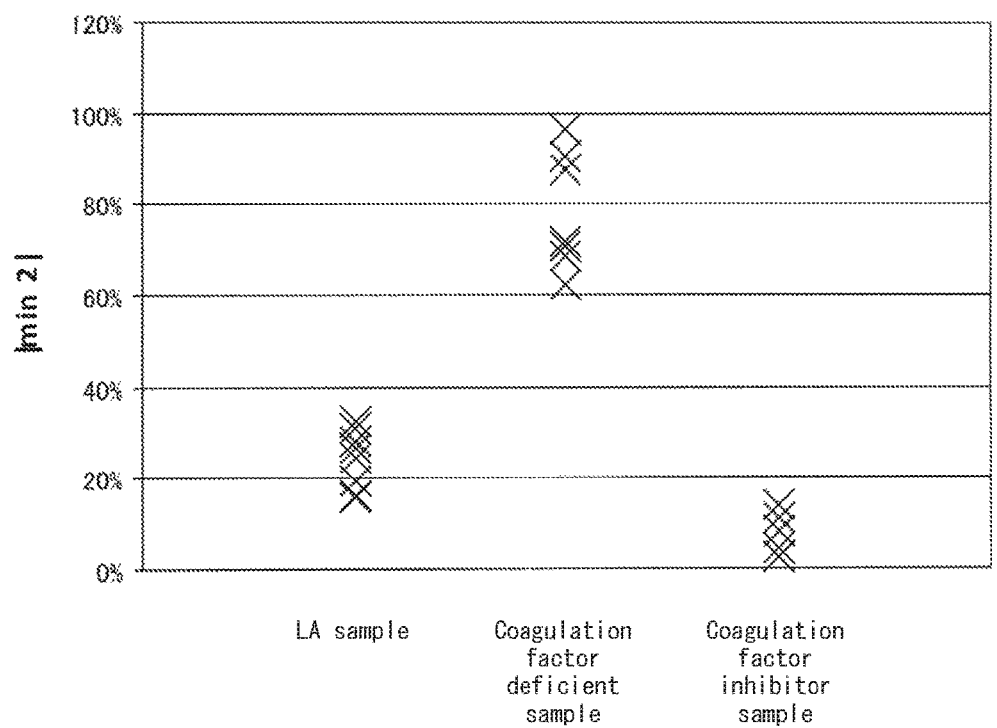
FIG. 12B is a graph showing the proportion of |min 2| of each subject plasma relative to the value of |min 2| of the normal plasma.
Figure 12C:
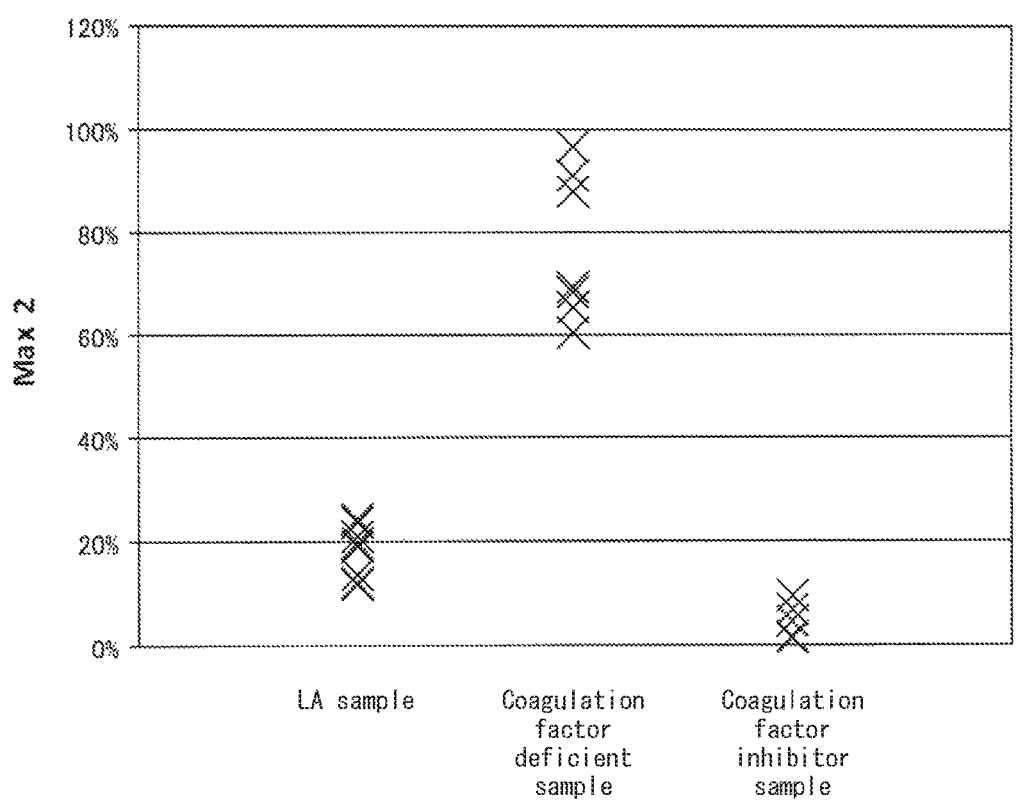
FIG. 12C is a graph showing the proportion of max 2 of each subject plasma relative to the value of max 2 of the normal plasma.

As shown in FIGS. 12A to 12C, with respect to each of |min 1|, |min 2|, and max 2, the group of coagulation-factor-deficient samples showed higher values than those of the group of LA positive samples and the group of coagulation-factor-inhibitor positive samples. Also with respect to each of |min 1|, |min 2|, and max 2, there is a gap between the minimum value of the group of coagulation-factor-deficient samples and the maximum values of the group of LA positive samples and the group of coagulation-factor-inhibitor positive samples. Thus, it is suggested that, for each parameter, a threshold can be set that separates coagulation-factor-deficient samples from LA positive samples and coagulation-factor-inhibitor positive samples. Further, for each of |min 1|, |min 2|, and max 2, the group of LA positive samples has higher values than those of the group of coagulation-factor-inhibitor positive samples. From these, it was shown that, on the basis of the parameters regarding derivative of clot waveform, it is possible to quantitatively distinguish coagulation-factor-deficient samples, LA positive samples, and coagulation-factor-inhibitor positive samples from one another. Since these parameters are quantitative indexes, it is considered that persons who are not experts can make a clear sample determination.

Comparative Example: Sample Determination by Cross-Mixing Test

In this Comparative Example, a cross-mixing test was conducted for each of coagulation-factor-deficient samples, LA positive samples, and coagulation-factor-inhibitor positive samples, and it was examined whether causes for coagulation abnormality could be distinguished on the basis of obtained graph patterns.

(1) Reagent and Sample

The reagent, the subject plasma, the normal plasma, and the control specimen for quality control used in this Comparative Example were the same as those used in Example 1.

(2) Measurement

In order to obtain immediate-type graph pattern, the normal plasma and the subject plasma were mixed at each of ratios of 9:1, 8:2, 5:5, 2:8, and 1:9, to obtain a mixed plasma. Then, the clotting times of the normal plasma, the subject plasma, and each of the prepared mixed plasmas were measured. Mixing of the plasma, preparation of the measurement specimens, and measurement of clotting time were performed by CS-2400 (Sysmex Corporation). In order to obtain delayed-type graph pattern, in the measurement, the normal plasma and the subject plasma were mixed manually at the ratios mentioned above, to obtain mixed plasmas.

Then, the normal plasma, the subject plasma, and each prepared mixed plasma were incubated at 37° C. for 2 hours. Then, preparation of the measurement specimens and measurement of clotting time were conducted by CS-2400 (Sysmex Corporation). The clotting time obtained for each measurement specimen was plotted on a graph whose X axis represents the mixing proportion of the normal plasma and the subject plasma and whose Y axis represents the clotting time.

(3) Analysis Result

Figure 13A:
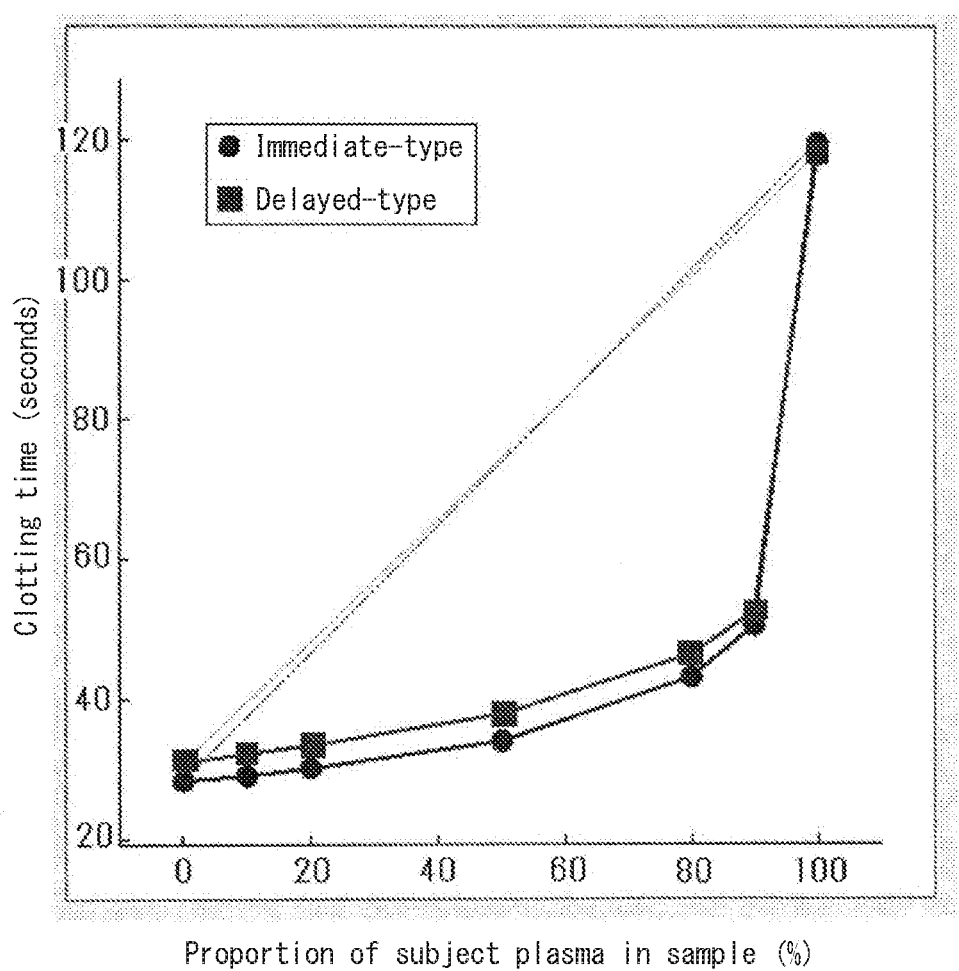
FIG. 13A is a graph showing immediate-type and delayed-type clotting times obtained when a cross-mixing test has been performed on a coagulation-factor-deficient sample.
Figure 13B:
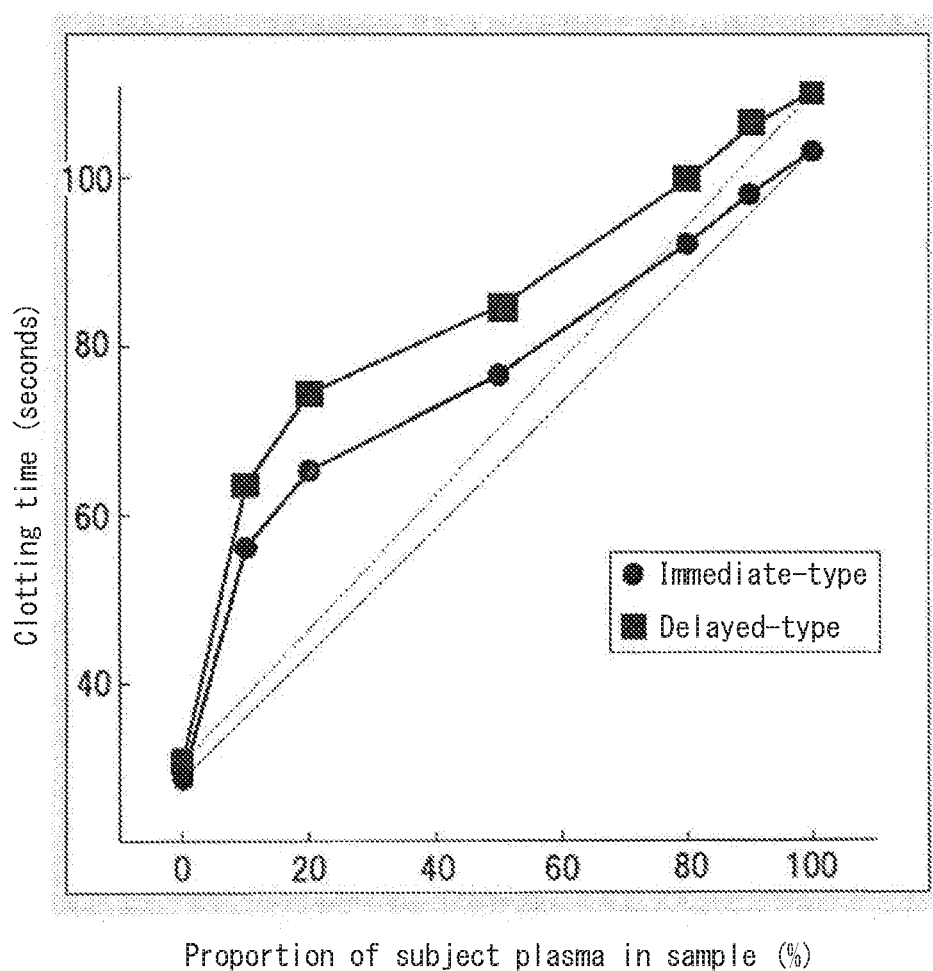
FIG. 13B is a graph showing immediate-type and delayed-type clotting times obtained when a cross-mixing test has been performed on an LA positive sample.
Figure 13C:
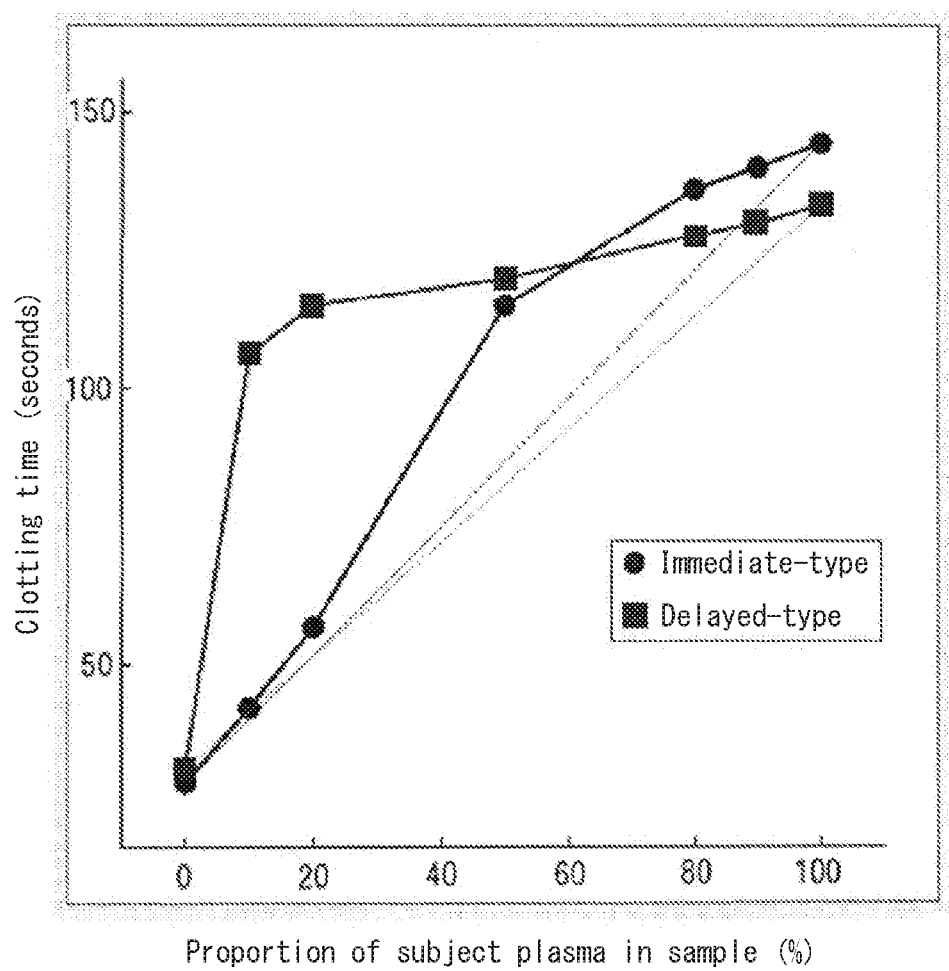
FIG. 13C is a graph showing immediate-type and delayed-type clotting times obtained when a cross-mixing test has been performed on a coagulation-factor-inhibitor positive sample.

With respect to the coagulation-factor-deficient samples, the LA positive samples, and the coagulation-factor-inhibitor positive samples, the immediate-type graph pattern and the delayed-type graph pattern are respectively shown in FIGS. 13A to 13C. As shown in FIGS. 13A to 13C, the coagulation-factor-deficient samples can be distinguished from the LA positive samples and the coagulation-factor-inhibitor positive samples, on the basis of the change in the immediate-type and delayed-type graph patterns. However, distinction among these based on the change in the graph patterns is not so quantitative, and the experimental procedure therefor is complicated. As shown in FIGS. 13B and 13C, the changes in graph patterns of the LA positive samples and the coagulation-factor-inhibitor positive samples are analogous to each other. Thus, distinction between these based on the change in the graph patterns has to be qualitative assessment. Thus, it is seen that making an appropriate determination is difficult for non-expert persons.

What is claimed is:

1. A blood sample determination method comprising:
   emitting light to a measurement specimen comprising a subject plasma, a normal plasma, and a clotting time measuring reagent;
   obtaining at least one parameter regarding a derivative of a clot waveform, on the basis of optical information obtained from the one measurement specimen, wherein the parameter is at least one selected from the group consisting of a maximum coagulation velocity (|min 1|), a maximum coagulation acceleration (|min 2|), and a maximum coagulation deceleration (max 2); and
   determining that the subject plasma is suspected to be a coagulation-factor-deficient plasma when a value of the parameter is greater than or equal to a threshold A, that the subject plasma is suspected to be a lupus anticoagulant (LA) when a value of the parameter is smaller than the threshold A and is greater than or equal to a threshold B which is smaller than the threshold A, and that the subject plasma is suspected to be a coagulation factor inhibitor when a value of the parameter is smaller than the threshold B.

2. The blood sample determination method of claim 1, wherein
   the optical information is an amount of scattered light, transmittance, or absorbance which has been measured continuously or intermittently, and the clot waveform is a waveform representing a temporal change in the amount of scattered light, the transmittance, or the absorbance.

3. The blood sample determination method of claim 1, further comprising preparing the mixed plasma by mixing a subject plasma and a normal plasma.

4. The blood sample determination method of claim 3, wherein
   in the step of determining,
   the value of |min 1| is compared with the first threshold and the fourth threshold in a case where |min 1| has been obtained, the value of |min 2| is compared with the second threshold and the fifth threshold in a case where |min 2| has been obtained, and the value of max 2 is compared with the third threshold and the sixth threshold in a case where max 2 has been obtained,
   when at least one of the values that have been obtained from among |min 1|, |min 2|, and max 2 is greater than or equal to the first, second, or third threshold corresponding to that value, it is determined that the subject plasma is suspected to be a coagulation-factor-deficient plasma,
   when all the values that have been obtained from among |min 1|, |min 2|, and max 2 are smaller than the first, second, or third thresholds corresponding to those values, respectively, and at least one of the values that have been obtained from among |min 1|, |min 2|, and max 2 is greater than or equal to the fourth, fifth, or sixth threshold corresponding to that value, it is determined that the subject plasma is suspected to be a plasma containing LA, and
   when all the values that have been obtained from among |min 1|, |min 2|, and max 2 are smaller than the fourth, fifth, or sixth thresholds corresponding to those values, respectively, it is determined that the subject plasma is suspected to be a plasma containing a coagulation factor inhibitor.

5. The blood sample determination method of claim 1, wherein
   the clotting time measuring reagent is a reagent for measuring at least one selected from the group consisting of prothrombin time, activated partial thromboplastin time, dilute prothrombin time, dilute activated partial thromboplastin time, kaolin clotting time, dilute Russell viper venom time, thrombin time, and dilute thrombin time.

6. The blood sample determination method of claim 1, comprising:
   emitting light to another measurement specimen obtained by mixing the subject plasma and the clotting time measuring reagent, to obtain optical information regarding an amount of light from the another measurement specimen; and
   obtaining a clotting time of the another measurement specimen, on the basis of the optical information obtained from the another measurement specimen, wherein
   in the step of determining, with respect to a subject plasma for which prolongation of the clotting time thereof has been observed, whether the subject plasma is suspected to be a coagulation-factor-deficient plasma is determined on the basis of the value of the obtained parameter.

7. The blood sample determination method of claim 6, comprising:
   determining whether the another measurement specimen has a prolonged clotting time, on the basis of the result of comparison of the obtained clotting time with a predetermined time.

8. The blood sample determination method of claim 1, wherein the threshold A comprises a first threshold, a second threshold and a third threshold; and the threshold B comprises a fourth threshold, a fifth threshold, and a sixth threshold.

9. A blood sample analyzer comprising:
   a measurement specimen preparation section configured to prepare a measurement specimen by mixing a plasma and a clotting time measuring reagent;

an optical information obtainment section configured to emit light to the prepared measurement specimen, to obtain optical information regarding an amount of light from the measurement specimen; and a controller, wherein the measurement specimen preparation section prepares a measurement specimen by mixing the reagent and a mixed plasma which is obtained by mixing a subject plasma and a normal plasma, and the controller is programmed to perform operations comprising:

obtaining, on the basis of the optical information, at least one parameter regarding a derivative of a clot waveform selected from the group consisting of maximum coagulation velocity (|min 1|), maximum coagulation acceleration (|min 2|), and maximum coagulation deceleration (max 2); and comparing a value of the parameter with a predetermined threshold A and a predetermined threshold B that is smaller than the threshold A, and outputting reference information regarding the subject plasma on the basis of a result of the comparison, wherein the reference information is that the subject plasma is suspected to be a coagulation-factor-deficient plasma when the value of the parameter is greater than or equal to the threshold A; the reference information is that the subject plasma is suspected to be a lupus anticoagulant (LA) when the value of the parameter is smaller than the threshold A and is greater than or equal to the threshold B; and the reference information is that the subject plasma is suspected to be a coagulation factor inhibitor when the value of the parameter is smaller than the threshold B.

10. The blood sample analyzer of claim 9, wherein the measurement specimen preparation section prepares another measurement specimen by mixing the subject plasma and the reagent, and the controller is programmed to perform operations comprising:

obtaining a clotting time on the basis of optical information of the another measurement specimen;

comparing the obtained clotting time with a predetermined time, and when the clotting time is longer than the predetermined time comparing the value of the parameter with the predetermined thresholds A and B; and outputting the reference information regarding the subject plasma in the another measurement specimen on the basis of a result of the comparison, wherein the reference information is that the subject plasma in the another measurement specimen is suspected to be a coagulation-factor-deficient plasma when the value of the parameter is greater than or equal to the threshold A; the reference information is that the subject plasma in the another measurement specimen is suspected to be a lupus anticoagulant (LA) when the value of the parameter is smaller than the threshold A and is greater than or equal to the threshold B; and the reference information is that the subject plasma in the another measurement specimen is suspected to be a coagulation factor inhibitor when the value of the parameter is smaller than the threshold B.

11. The blood sample analyzer of claim 9, further comprising a display unit configured to display an analysis result, wherein the controller is further programmed to perform an operation comprising outputting the reference information regarding the subject plasma to the display unit.

12. The blood sample analyzer of claim 9, wherein the optical information is an amount of scattered light, transmittance, or absorbance which has been measured continuously or intermittently, and a clot waveform is a waveform representing temporal change in the amount of scattered light, the transmittance, or the absorbance.

13. The blood sample analyzer of claim 9, wherein the threshold A comprises a first threshold, a second threshold and a third threshold; and the threshold B comprises a fourth threshold, a fifth threshold, and a sixth threshold.

14. The blood sample analyzer of claim 13, wherein the controller is further programmed to perform operations comprising:

comparing the value of |min 1| with the first threshold and the fourth threshold in a case where |min 1| has been obtained, comparing the value of |min 2| with the second threshold and the fifth threshold in a case where |min 2| has been obtained, and comparing the value of max 2 with the third threshold and the sixth threshold in a case where max 2 has been obtained;

when at least one of the values that have been obtained from among |min 1|, |min 2|, and max 2 is greater than or equal to the first, second, or third threshold corresponding to that value, outputting reference information indicating that the subject plasma is suspected to be a coagulation-factor-deficient plasma;

when all the values that have been obtained from among |min 1|, |min 2|, and max 2 are smaller than the first, second, or third thresholds corresponding to those values, respectively, and at least one of the values that have been obtained from among |min 1|, |min 2|, and max 2 is greater than or equal to the fourth, fifth, or sixth threshold corresponding to that value, outputting reference information indicating that the subject plasma is suspected to be a plasma containing LA; and when all the values that have been obtained from among |min 1|, |min 2|, and max 2 are smaller than the fourth, fifth, or sixth thresholds corresponding to those values, respectively, outputting reference information indicating that the subject plasma is suspected to be a plasma containing a coagulation factor inhibitor.

15. The blood sample analyzer of claim 9, wherein the clotting time measuring reagent is a reagent for measuring at least one selected from the group consisting of prothrombin time, activated partial thromboplastin time, dilute prothrombin time, dilute activated partial thromboplastin time, kaolin clotting time, dilute Russell viper venom time, thrombin time, and dilute thrombin time.

16. A blood sample analyzer comprising:

a measurement specimen preparation section configured to prepare a measurement specimen by mixing a plasma and a clotting time measuring reagent;

an optical information obtainment section configured to emit light to the prepared measurement specimen, to obtain optical information regarding an amount of light from the measurement specimen; and a controller, wherein the measurement specimen preparation section prepares a first measurement specimen by mixing a subject plasma and the reagent, and a second measurement specimen by mixing the reagent and a mixed plasma which is obtained by mixing the subject plasma and a normal plasma, and the controller is programmed to perform operations comprising:

obtaining a clotting time on the basis of optical information of the first measurement specimen, and obtaining, on the basis of optical information of the second measurement specimen, at least one parameter regarding a derivative of a clot waveform selected from the group consisting of maximum coagulation velocity (|min 1|), maximum coagulation acceleration (|min 2|), and maximum coagulation deceleration (max 2);

comparing the obtained clotting time with a predetermined time, and comparing a value of the parameter with a predetermined threshold A and a predetermined threshold B that is smaller than the threshold A when the clotting time is longer than the predetermined time; and outputting reference information regarding the subject plasma on the basis of a result of the comparison, wherein the reference information is that the subject plasma is suspected to be a coagulation-factor-deficient plasma when the value of the parameter is greater than or equal to the threshold A; the reference information is that the subject plasma is suspected to be a lupus anticoagulant (LA) when the value of the parameter is smaller than the threshold A and is greater than or equal to the threshold B; and the reference information is that the subject plasma is suspected to be a coagulation factor inhibitor when the value of the parameter is smaller than the threshold B.

17. The blood sample analyzer of claim 16, further comprising
a display unit configured to display an analysis result, wherein
the controller is further programmed to perform an operation comprising
outputting the reference information regarding the subject plasma to the display unit.

18. The blood sample analyzer of claim 16, wherein
the optical information is an amount of scattered light, transmittance, or absorbance which has been measured continuously or intermittently, and a clot waveform is a waveform representing temporal change in the amount of scattered light, the transmittance, or the absorbance.

19. The blood sample analyzer of claim 16, wherein the threshold A comprises a first threshold, a second threshold and a third threshold; and the threshold B comprises a fourth threshold, a fifth threshold, and a sixth threshold.

20. The blood sample analyzer of claim 19, wherein
the controller is further programmed to perform operations comprising:

comparing the value of |min 1| with the first threshold and the fourth threshold in a case where |min 1| has been obtained, comparing the value of |min 2| with the second threshold and the fifth threshold in a case where |min 2| has been obtained, and comparing the value of max 2 with the third threshold and the sixth threshold in a case where max 2 has been obtained;

when at least one of the values that have been obtained from among |min 1|, |min 2|, and max 2 is greater than or equal to the first, second, or third threshold corresponding to that value, outputting reference information indicating that the subject plasma is suspected to be a coagulation-factor-deficient plasma;

when all the values that have been obtained from among |min 1|, |min 2|, and max 2 are smaller than the first, second, or third thresholds corresponding to those values, respectively, and at least one of the values that have been obtained from among |min 1|, |min 2|, and max 2 is greater than or equal to the fourth, fifth, or sixth threshold corresponding to that value, outputting reference information indicating that the subject plasma is suspected to be a plasma containing LA; and when all the values that have been obtained from among |min 1|, |min 2|, and max 2 are smaller than the fourth, fifth, or sixth thresholds corresponding to those values, respectively, outputting reference information indicating that the subject plasma is suspected to be a plasma containing a coagulation factor inhibitor.

21. The blood sample analyzer of claim 16, wherein
the clotting time measuring reagent is a reagent for measuring at least one selected from the group consisting of prothrombin time, activated partial thromboplastin time, dilute prothrombin time, dilute activated partial thromboplastin time, kaolin clotting time, dilute Russell viper venom time, thrombin time, and dilute thrombin time.

* * * * *